(12) United States Patent
Hart et al.

(10) Patent No.: US 7,189,249 B2
(45) Date of Patent: Mar. 13, 2007

(54) TRACTION TROCAR APPARATUS AND METHOD

(75) Inventors: Charles C. Hart, Summerville, SC (US); Edward D. Pingleton, Laguna Niguel, CA (US); John R. Brustad, Dana Point, CA (US); Nabil Hilal, Laguna Niguel, CA (US); Raffi Pinedjian, Fountain Valley, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 282 days.

(21) Appl. No.: 10/477,330

(22) PCT Filed: May 11, 2001

(86) PCT No.: PCT/US01/15390

§ 371 (c)(1),
(2), (4) Date: Nov. 5, 2003

(87) PCT Pub. No.: WO02/091930

PCT Pub. Date: Nov. 21, 2002

(65) Prior Publication Data

US 2004/0143281 A1    Jul. 22, 2004

(51) Int. Cl.
*A61B 17/34* (2006.01)
(52) U.S. Cl. .................... 606/185; 604/264
(58) Field of Classification Search ............... 606/204, 606/167, 185; 600/203, 204, 206, 158; 604/206, 604/158, 171, 523, 26
See application file for complete search history.

(56) References Cited

U.S. PATENT DOCUMENTS 2,704,071 A    3/1955   Becker
5,066,288 A   11/1991   Deniega
5,261,891 A   11/1993   Brinkerhoff
5,263,969 A   11/1993   Phillips
5,320,611 A    6/1994   Bonutti
5,407,427 A    4/1995   Zhu
5,443,484 A    8/1995   Kirsch
5,577,993 A   11/1996   Zhu
5,676,670 A   10/1997   Kim
5,688,286 A   11/1997   Yoon (Continued)

FOREIGN PATENT DOCUMENTS

WO        WO 00 48649 A       8/2000

*Primary Examiner*—(Jackie) Tan-Uyen Ho
*Assistant Examiner*—Natalie Pous
(74) *Attorney, Agent, or Firm*—David G. Majdali; Richard L. Myers

(57) ABSTRACT

The trocar system includes a cannula insertable through a body wall using an obturator having a distal tip. A traction tread disposed interiorly of the obturator inverts at the distal tip and extends proximally along the outer surface of the obturator or cannula. At the distal tip the tread can facilitate parting rather than cutting the tissue. Along the outer surface, the tread can engage the tissue to pull it proximally along the advancing obturator. This produces counter forces which can result in a net proximal force facilitating distention of the abdominal wall and separation of the abdominal wall from internal organs. The traction tread can be axially and/or radially continuous. An associated method of operation includes the steps of contacting the body wall with the traction tread at the distal tip, and engaging the body wall with the traction tread along wall portions facing the outer surface.

5 Claims, 22 Drawing Sheets

U.S. PATENT DOCUMENTS

| | | |
|---|---|---|
| 5,797,920 A | 8/1998 | Kim |
| 5,827,319 A | 10/1998 | Carlson |
| 6,007,521 A * | 12/1999 | Bidwell et al. ............. 604/264 |
| 6,080,174 A | 6/2000 | Dubrul |
| 6,093,173 A | 7/2000 | Balceta |
| 6,171,282 B1 | 1/2001 | Ragsdale |
| 2001/0044595 A1 * | 11/2001 | Reydel et al. ........... 604/98.02 |

* cited by examiner

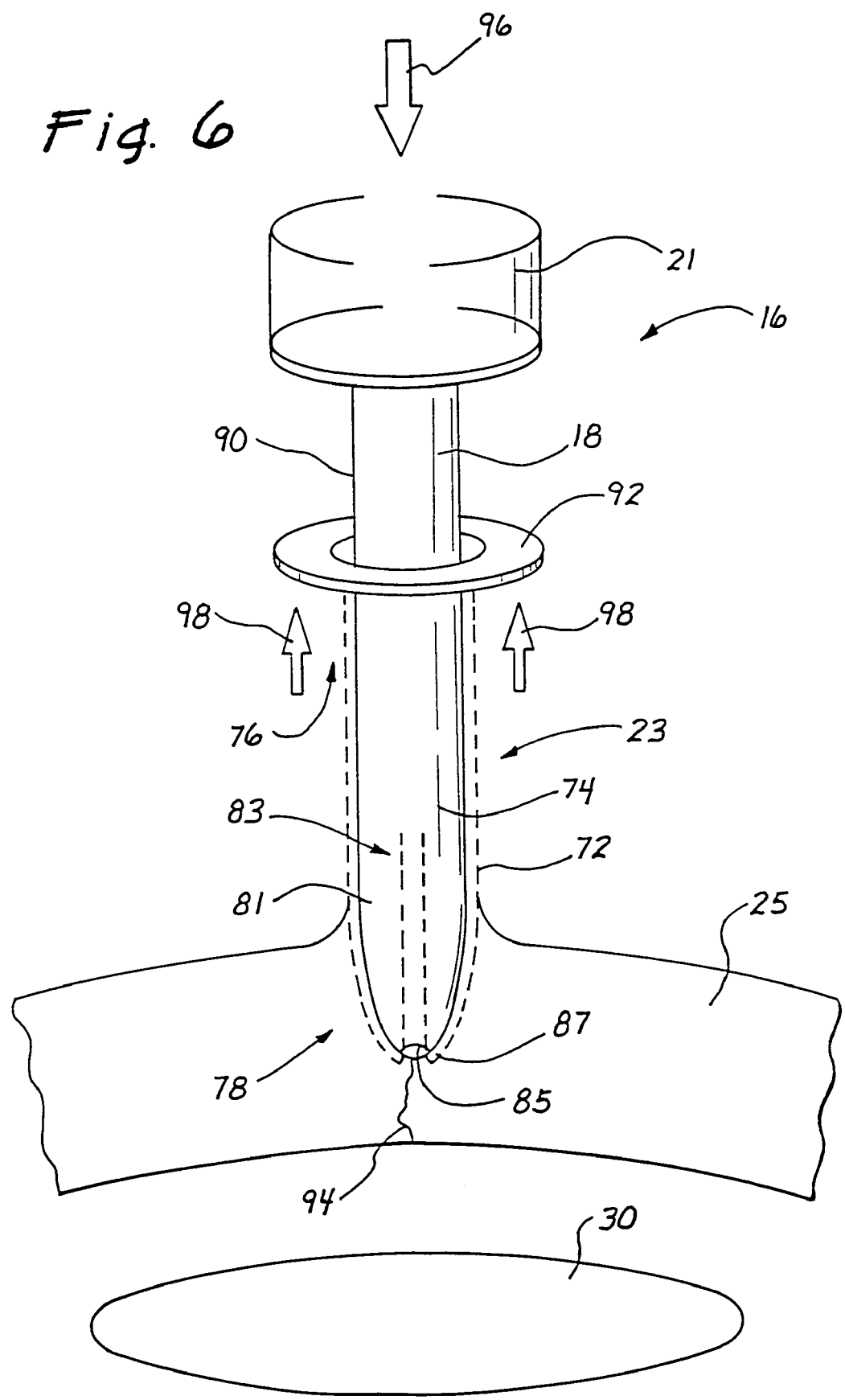

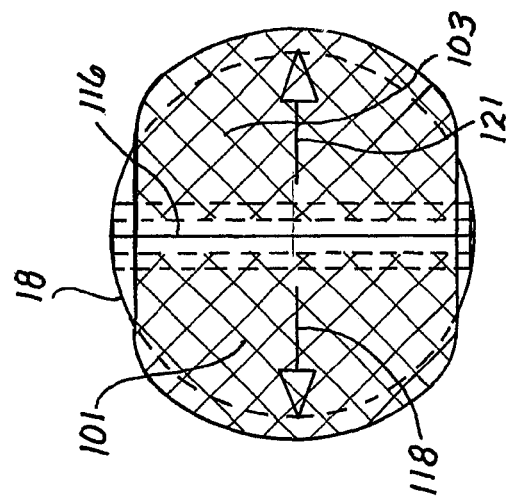
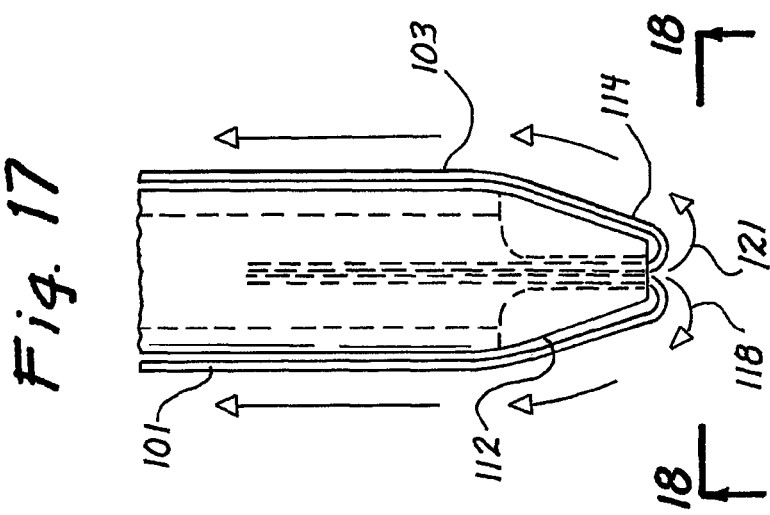
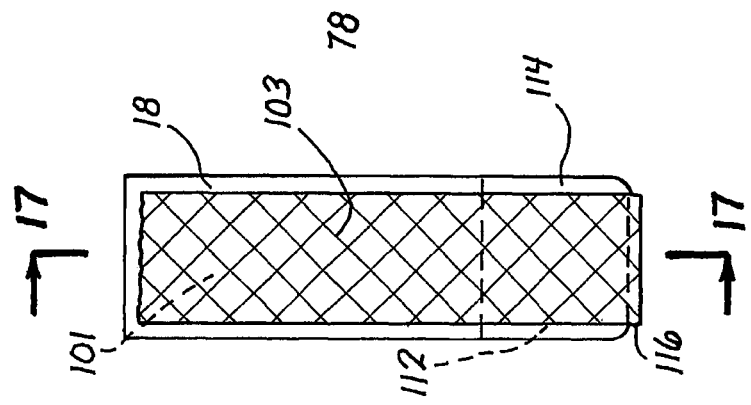

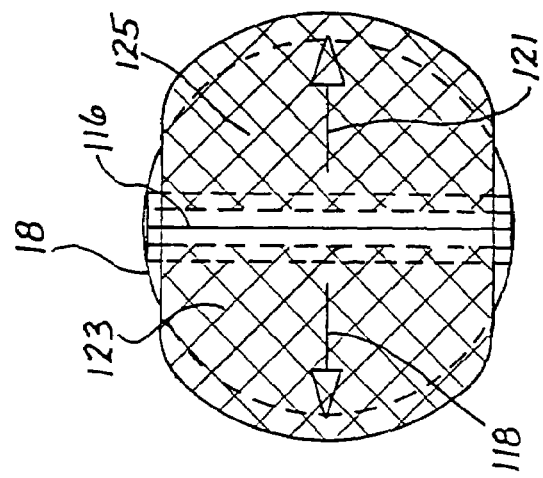
Fig. 21
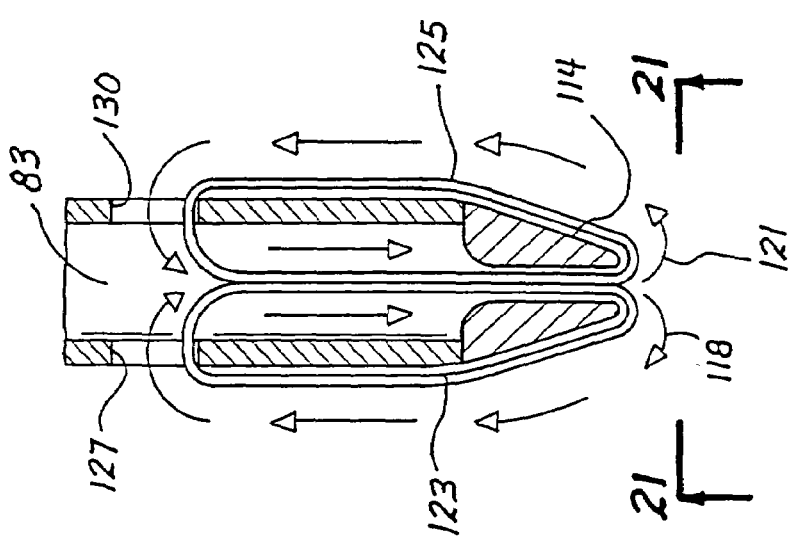
Fig. 20
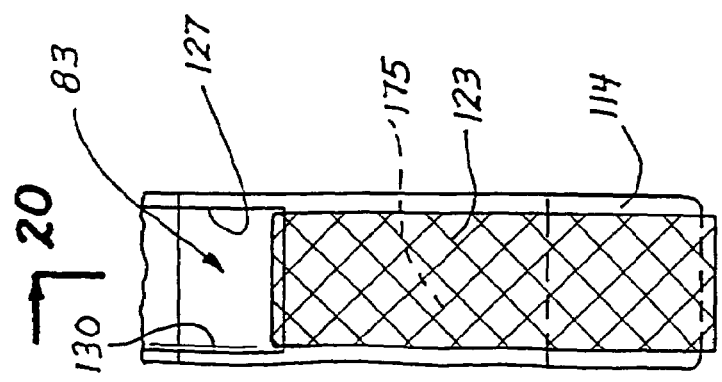
Fig. 19

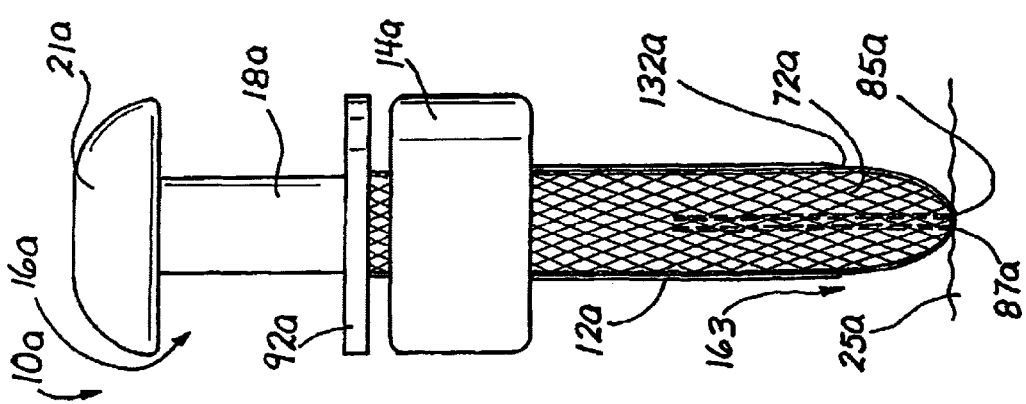

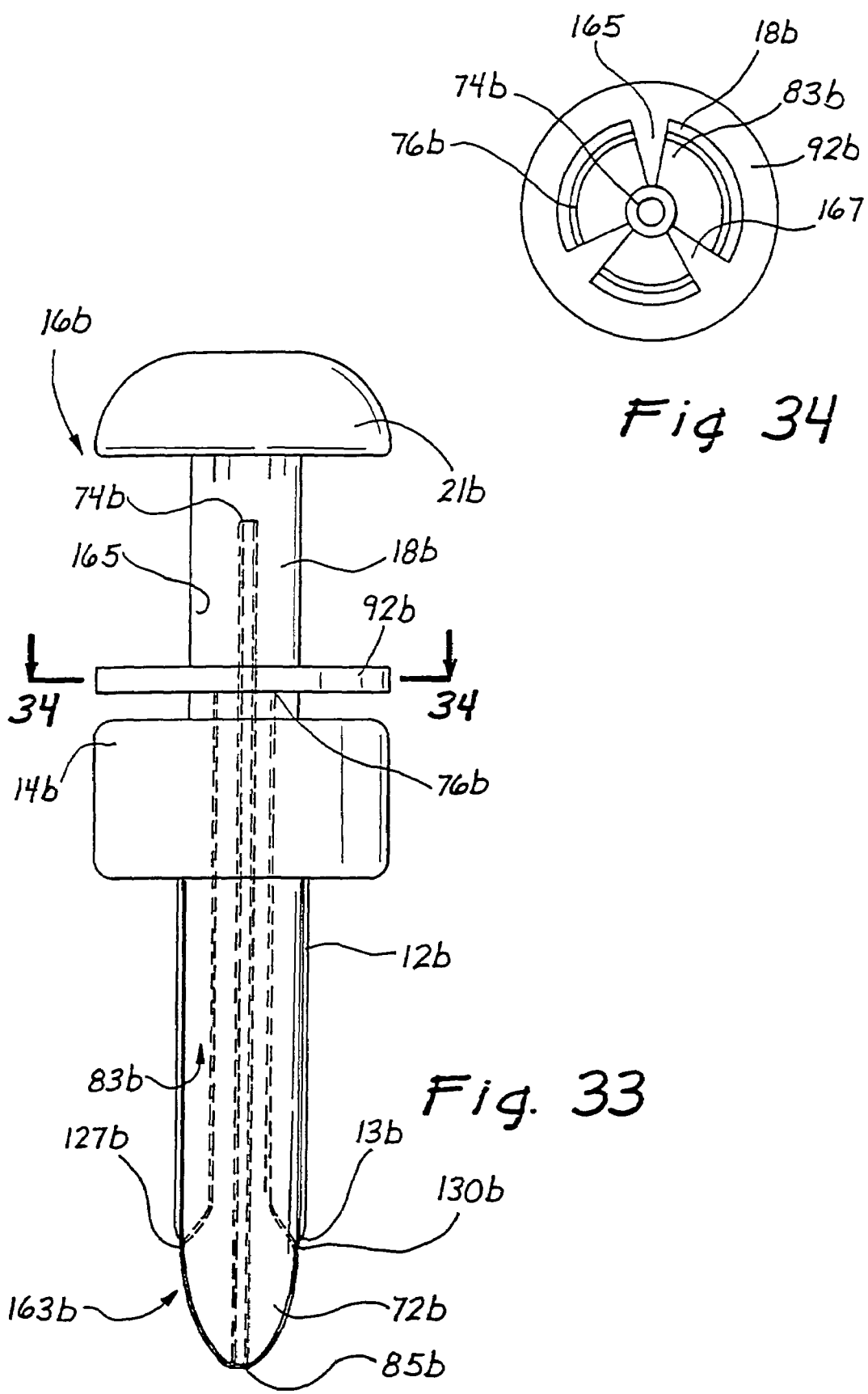

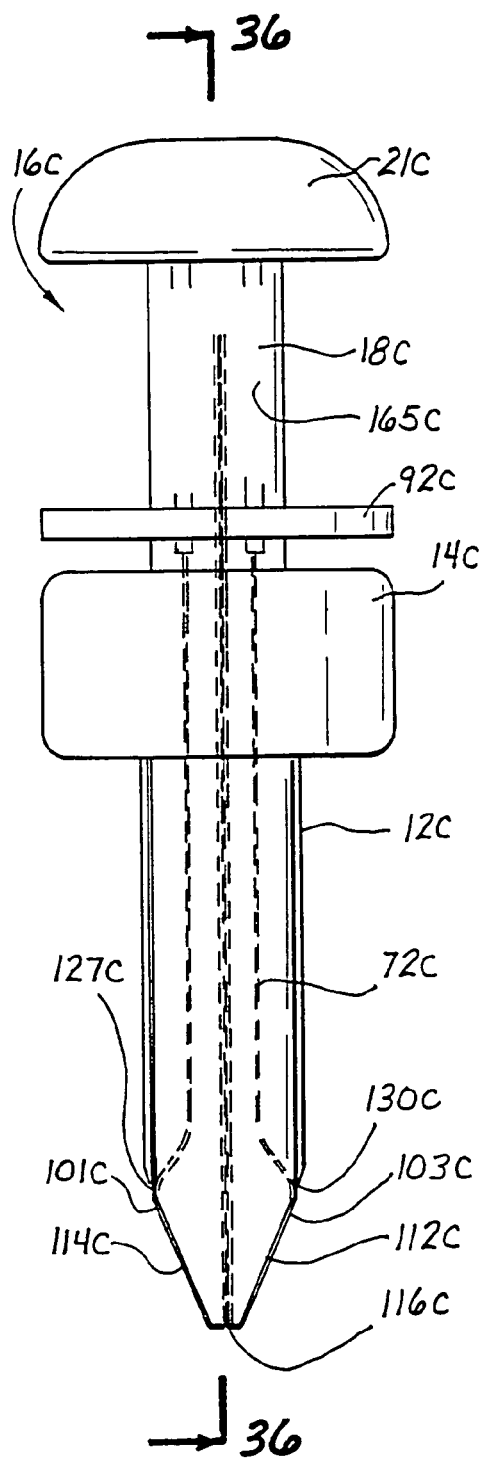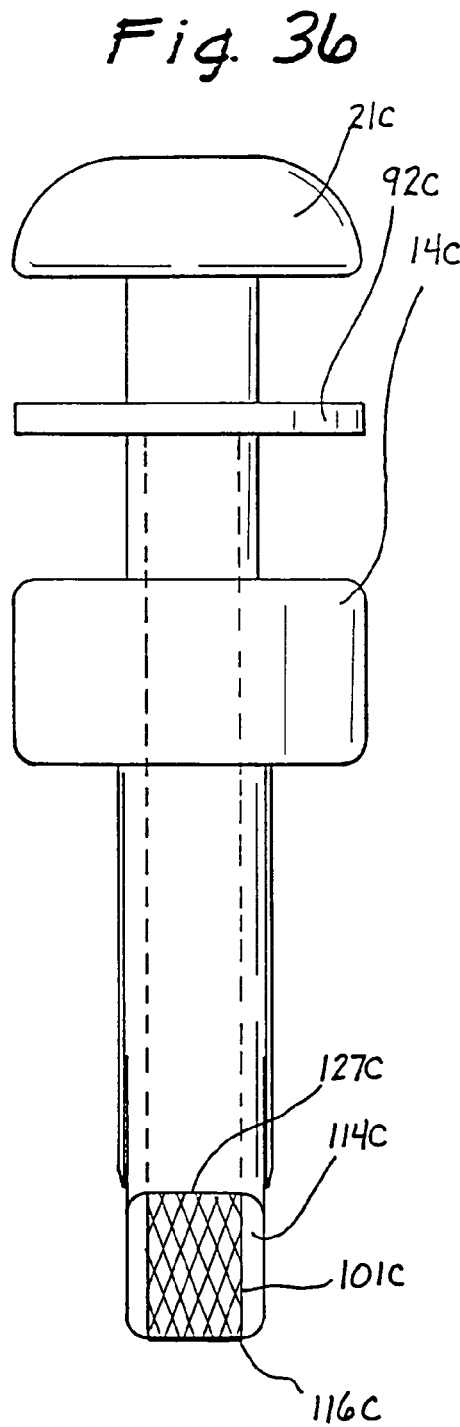
Fig. 35
Fig. 36

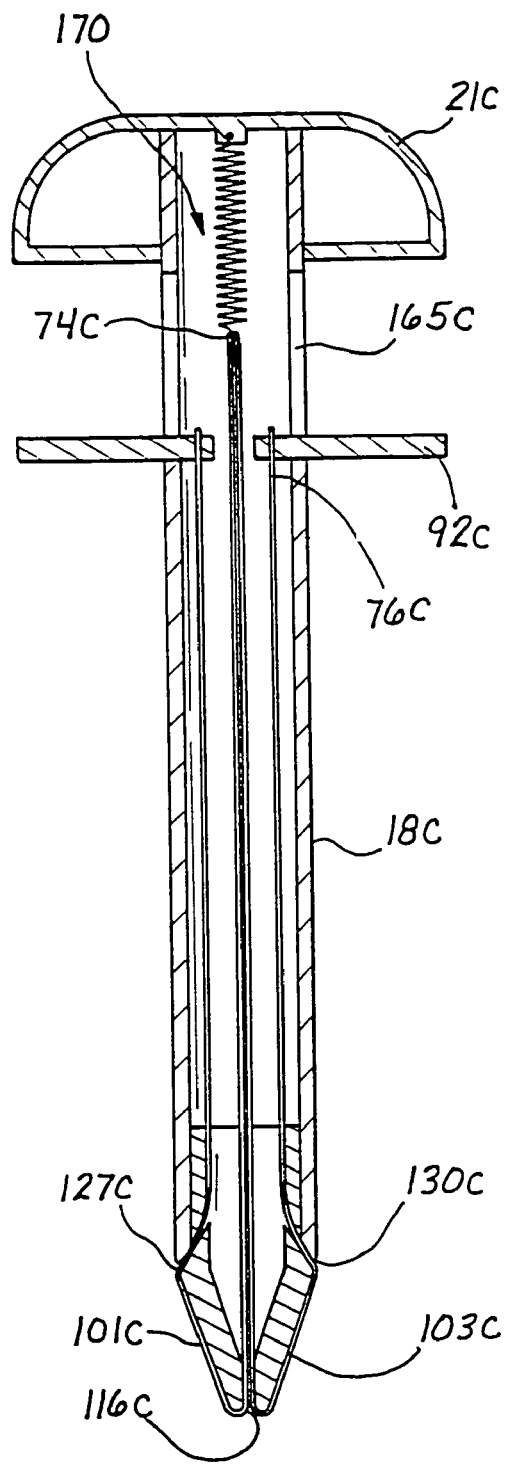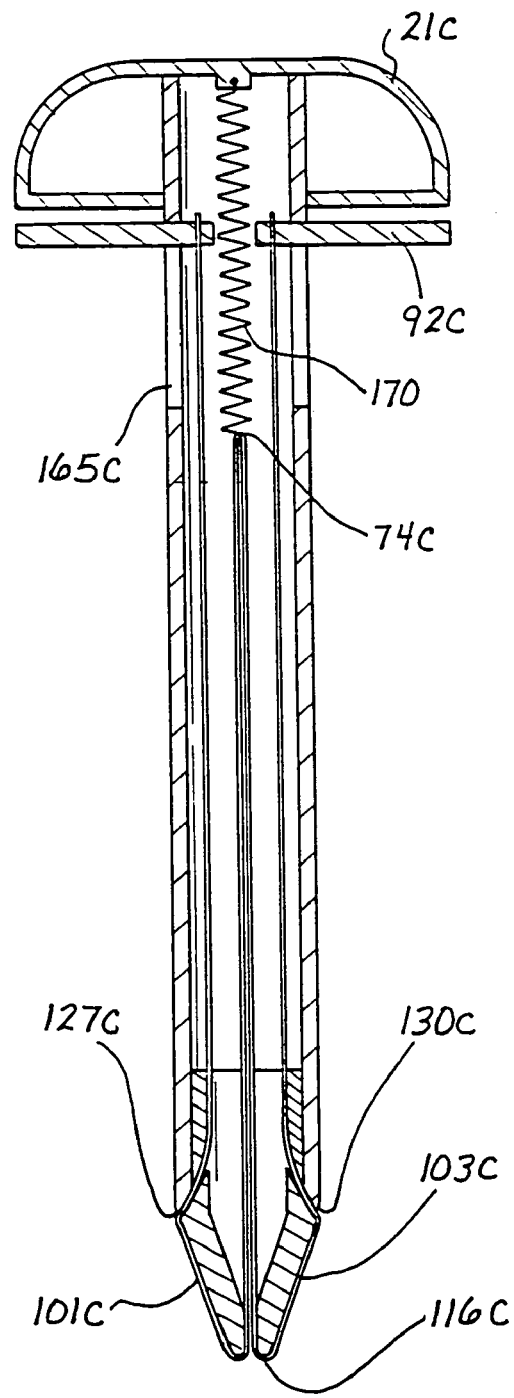
Fig. 37
Fig. 38

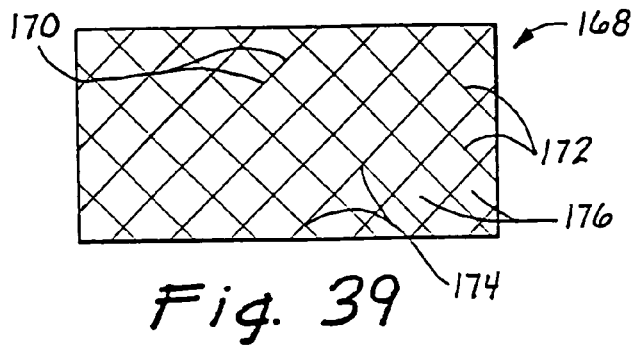
Fig. 39
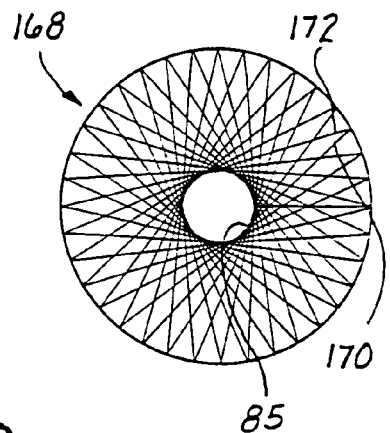
Fig. 43
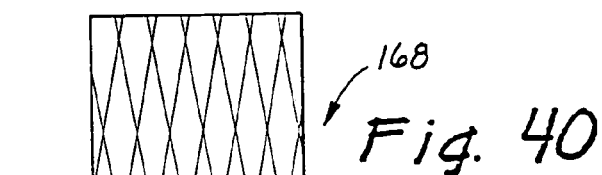
Fig. 40
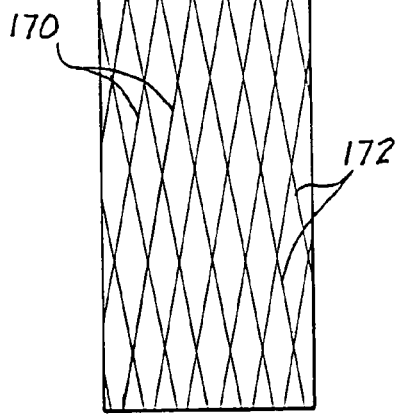
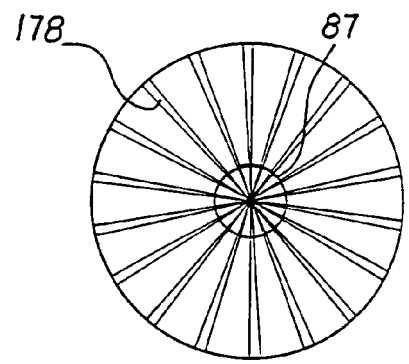
Fig. 42
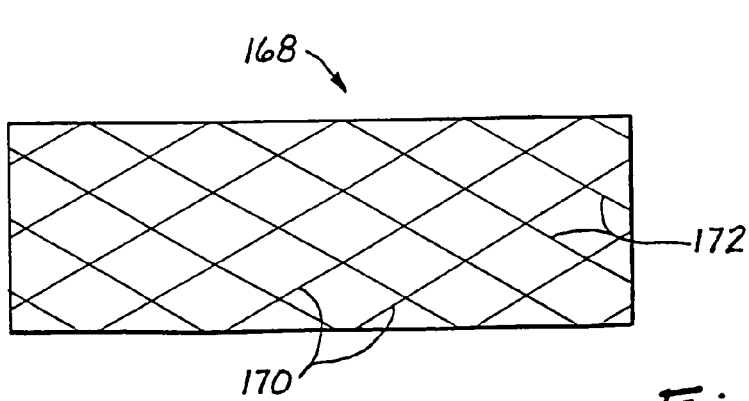
Fig. 41

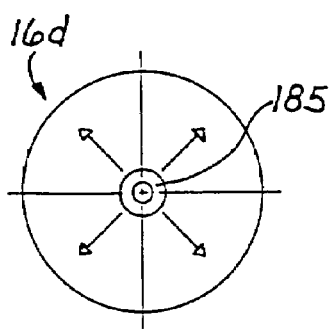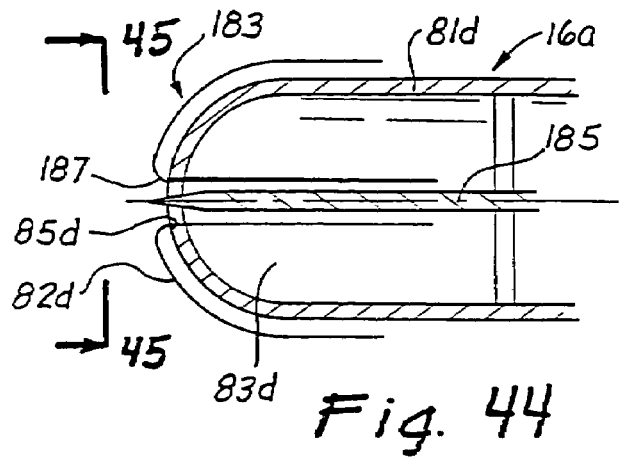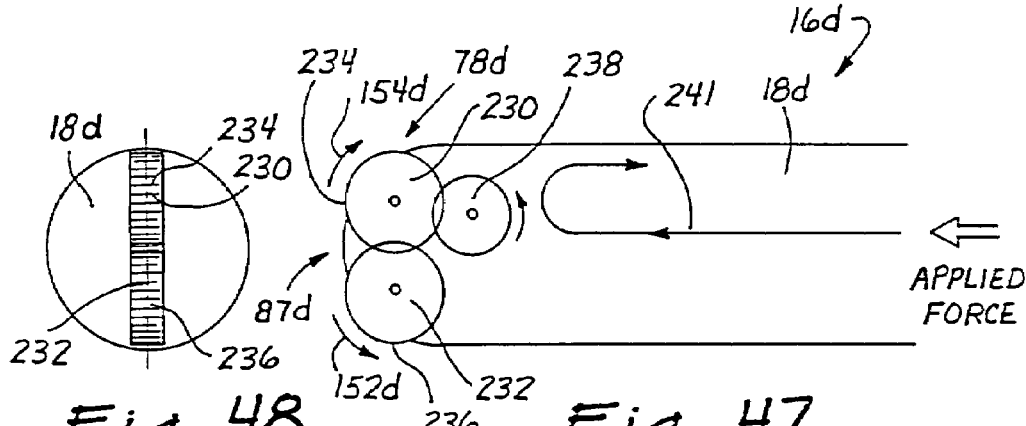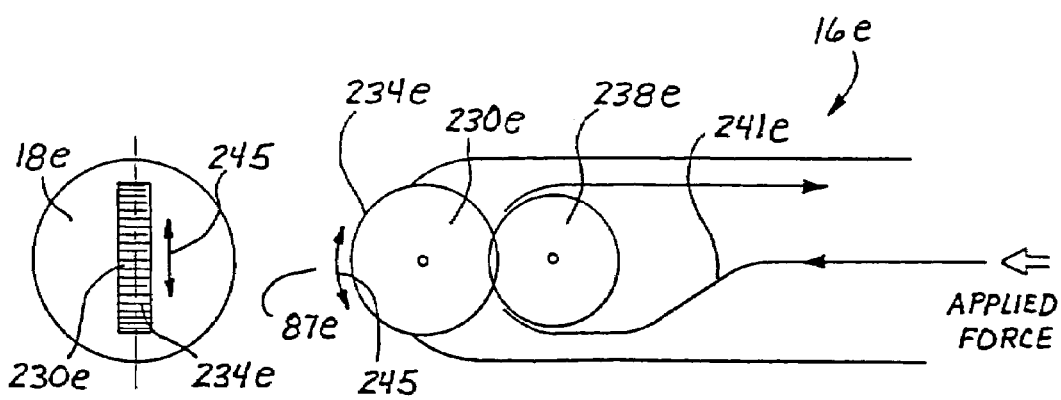

TRACTION TROCAR APPARATUS AND METHOD

BACKGROUND OF THE INVENTION

1. Field of Invention

This invention relates generally to trocar systems and more specifically to obturator apparatus and methods for placing a trocar cannula across a body wall.

2. Discussion of the Prior Art and Related Technology

It is generally well known that holes can be created through body tissue either by cutting the tissue or by mechanically parting the tissue along lines of weakness. Where tissue is cut, it is severed along a line, which is determined by the direction of the cutting implement. Where tissue is parted, it separates along natural tissue planes such as those defined by muscle fibers or differing layers of tissue such as skin and muscle. Tissue that is mechanically separated tends to heal better than tissue that is cut with tissue that is mechanically separated the healing process requires only that the affected tissues re-approximate each other with cut tissue, and in particular muscle fibers, the healing process must reconstruct the damaged tissue, often with resultant scaring and incomplete reconstruction. It has been shown for laparoscopic surgery in particular, that trocar wound sites of 10 millimeters in diameter and higher, made by cutting obturators, require suturing to prevent incisional hernias from occurring. It has also been shown that where the same size would site is created by expanding or parting the wound from a cut of 3 millimeters, for example, that the wound site does not require stitching and tends to heal faster.

For laparoscopic surgery there is a requirement that instrument ports in the form of cannulas be placed in the patient's abdominal wall. These cannulas are then used as access ports for the surgeon to place instruments such as scissors and graspers. In the past these cannulas have been introduced by using a sharp cutting obturator, placed within the cannula, to cut a line or hole for advancing the cannula through the abdominal wall. The obturator is then removed from the cannula and the cannula is left in place for the duration of the surgery.

For most surgeries the cutting obturator is only used after the abdomen has been insufflated with carbon dioxide gas. There is then separation between the abdominal wall and the underlying anatomical structures and organs. Even with this separation, however, there is a risk that the patient will be injured by the sharp cutting tip of the obturator as it breaks through the abdominal wall. To help resolve this issue a variety of mechanical shielding mechanisms have been employed to cover the cutting element once it breaks through the abdominal wall. It has been noted and observed that even with these mechanical shield mechanisms that the risk is not completely eliminated and that the rigid shields themselves can cause damage to internal organs and structures.

Other methods have been used as well. For example, optical trocars have been provided with a clear plastic cutting tip. This allows the surgeon to view the tissue layers as they are cut, and in principle to better control the timing of insertion forces. These plastic tips, however, are not as sharp as the metal bladed variety and therefore require a higher insertion force which in turn increase abdominal wall distortion. This distortion or tenting brings the obturator tip into closer proximity with the internal organs and increases the chances for potential damage. The wound created by such a device is still a cut and not a mechanical separation, as it still suffers from the above-mentioned disadvantages.

Another manufacturer employs a multistage system whereby a sheath is inserted over a veress needle. The needle is then removed and a conical obturator, placed inside a cannula, is inserted through the sheath thereby expanding it to the desired cannula size. The obturator is then removed leaving the cannula in place. This offers the advantage of a smaller initial incision with the veress needle. However, the needle still presents a risk to internal organs, and the system is more expensive and complex than those associated with the cutting obturator devices.

In all of these systems of the past, a cutting element is employed to either create the final size of the wound site or to make a smaller initial wound site that is then expanded to the final size. The use of sharp cutting elements common to all systems presents an unavoidable risk to the patient.

SUMMARY OF THE INVENTION

These deficiencies of the prior art are overcome with the present invention which provides for the parting rather than cutting of tissue, and, the use of opposing radial forces which precede the tip of the obturator shaft. After the tissue is parted, it is drawn proximally along the outer surface of the shaft as the shaft is moved distally through the body wall. The resulting counter forces can produce a net proximal force on the body wall with a minimal distal or penetration force.

In a preferred embodiment a tubular mesh sleeve is initially disposed in the hollow shaft of the obturator. This sleeve is pulled out of a hole at the tip of the obturator shaft and drawn radially and proximally along the outer surface of the shaft. The mesh sleeve inverts at the distal tip facilitating its movement interiorly of the shaft and its traction with the parted tissue exteriorly of the shaft.

In one aspect of the invention, an apparatus is provided for creating an opening through body tissue. The apparatus includes a shaft having an axis and a channel extending axially between a proximal end and a distal end. The shaft has a distal tip and a hole in the tip communicating with the channel of the shaft. Portions of the tip define a leading surface of the tip. Means is disposed along this leading surface and is moveable relative to the tip for creating generally opposing forces on the body tissue which tend to part the body tissue and thereby create the opening through the body tissue.

In another aspect of the invention, a surgical instrument is used for creating an opening through an abdominal wall retaining internal organs. The instrument includes a shaft having an outer surface and a tip. A sheath initially contacting the body tissue generally at a point extends proximally from the point along the outer surface of the shaft. The shaft is operable to create a distal force on the body tissue while the sheath is operable to create a proximal force on the body tissue. The proximal force is greater than the distal force in order to create a net proximal force on the abdominal wall tending to separate the abdominal wall from the internal organs as the opening is created.

In another aspect of the invention, a flexible sheath having a tubular configuration extends from an axial channel of the shaft through the distal tip of the shaft. A handle is attached to the sheath exteriorly of the shaft and is moveable proximally relative to the shaft to withdraw the sheath from the channel and to progressively invert the sheath at the tip of the shaft.

In another aspect of the invention, the shaft of the surgical instrument has a tubular configuration with an outer surface, an axial channel, and a distal tip. At least one flexible traction tread is carried within the axial channel and extends outwardly of the shaft at the distal tip. A handle attached to the traction tread exteriorly of the shaft is moveable proximally to withdraw the traction tread distally through the distal tip.

An associated method of operation includes even further aspects of the invention. For example, a method for creating an opening in body tissue includes the steps of providing opposing traction treads extending from the axial channel of the shaft outwardly through the hole in the tip of the shaft. The body tissue is contacted with the traction treads at the tip of the shaft and the traction treads are moved radially outwardly from the hole in the tip. During this moving step, the body tissue is engaged at the tip to produce parting forces on the body tissue tending to separate the body tissue and thereby create the opening through the body tissue.

In another method of operation, first and second cannulas are inserted through body tissue by providing an obturator having a shaft with an outer surface and a traction tread moveable relative to the outer surface. Placing the obturator in the first cannula, the body tissue is engaged with the tread and the tread is moved relative to the outer surface of the shaft to facilitate penetration of the body tissue by the shaft and the first cannula. The obturator is then removed from the first cannula and placed in the second cannula where again the traction thread engages the tissue and facilitates penetration of the body tissue by the shaft in the second cannula. Removing the obturator from the second cannula leaves both the first cannula and the second cannula operatively disposed across the body wall.

In another method associated with the invention, removal of a trocar cannula from a body wall is facilitated by placing a mesh sleeve between the cannula and the body wall. The sleeve is provided with properties which exert a radial force on the cannula tending to resist removal of the cannula from the body wall. However, an axial force can be applied to the sleeve to reduce the radial force of the sleeve on the cannula. During this step of applying the axial force, the cannula can be removed from the body wall.

In a method for inserting an obturator, the obturator is provided with a shaft having an outer surface and a traction tread moveable along the outer surface of the shaft. The tread is carried within the shaft. As the obturator is moved through the body wall, a first force is applied to the obturator in a first direction and a second force is applied to the obturator in a second generally opposing direction. As the obturator is moved distally relative to the body wall, it engages wall portions which face the outer surface of the shaft and pulls those wall portions proximally along the shaft.

These and other features and advantages of the invention will be better understood with reference to preferred embodiments of the concept and reference to the associated drawings.

DESCRIPTION OF THE DRAWINGS

FIG. 6 is a side elevation view of the system of the present invention including an inverting sheath operable with counter forces which can produce a net proximal force on the body wall;

FIG. 16 is a side elevation view of a further embodiment of the obturator wherein opposing traction treads are axially continuous;

FIG. 17 is an axial cross section view taken along line 17—17 of FIG. 16;

FIG. 18 is an end view taken along line 18—18 of FIG. 17;

FIG. 19 is a front elevation view similar to FIG. 16 and illustrating an embodiment including axially continuous traction treads;

FIG. 20 is an axial cross section view taken along lines 19—19;

FIG. 21 is an end view taken along lines 21—21 of FIG. 20;

FIGS. 29–32 illustrate a series of side elevation views showing progressive steps for operating an embodiment wherein the inverting sheath is disposed outwardly of the obturator but inwardly of the trocar cannula;

FIG. 33 is a side elevation view of a blunt-nose obturator having windows to facilitate the return of the inverting sheath to an interior channel of the obturator;

FIG. 34 is a cross section view taken along lines 34—34 of FIG. 33;

FIG. 35 is a side elevation view similar to FIG. 33 and showing an obturator tip with converging planes;

FIG. 36 is a front elevation view taken along lines 35—35 of FIG. 34;

FIG. 37 is an axial cross section view of an obturator similar to that of FIG. 34 and including a biasing means for returning the inverting sheath to its initial position;

FIG. 38 is an axial cross section view similar to FIG. 37 and illustrating the biasing means stretched to a final position of the inverting sheath;

FIG. 39 illustrates a fabric adapted for use as a traction tread or sheath, the fabric being illustrated in a normal state;

FIG. 40 is a side elevation view of the mesh of FIG. 39 axially stretched;

FIG. 41 is a side elevation view of the mesh of FIG. 39 radially stretched;

FIG. 42 is an end view of the traction-sheath formed of the mesh of FIG. 39;

FIG. 43 is an end view similar to FIG. 41 of the inverting sheath forming pleats to provide texture for traction;

FIG. 44 is a side elevation view of a further embodiment of the obturator including a blunt tip with a conical point for microscopic puncture;

FIG. 45 is an end view taken along lines 45—45 of FIG. 44;

FIG. 47 is a schematic axial cross section view of a further embodiment including gears with circumferential teeth;

FIG. 48 is an end view of the embodiment illustrated in FIG. 47;

FIG. 49 is a schematic axial cross section view of a further embodiment including a single oscillating gear; and FIG. 50 is an end view of the embodiment of FIG. 49.

DESCRIPTION OF PREFERRED
EMBODIMENTS AND BEST MODE OF THE
INVENTION

Figure 1:
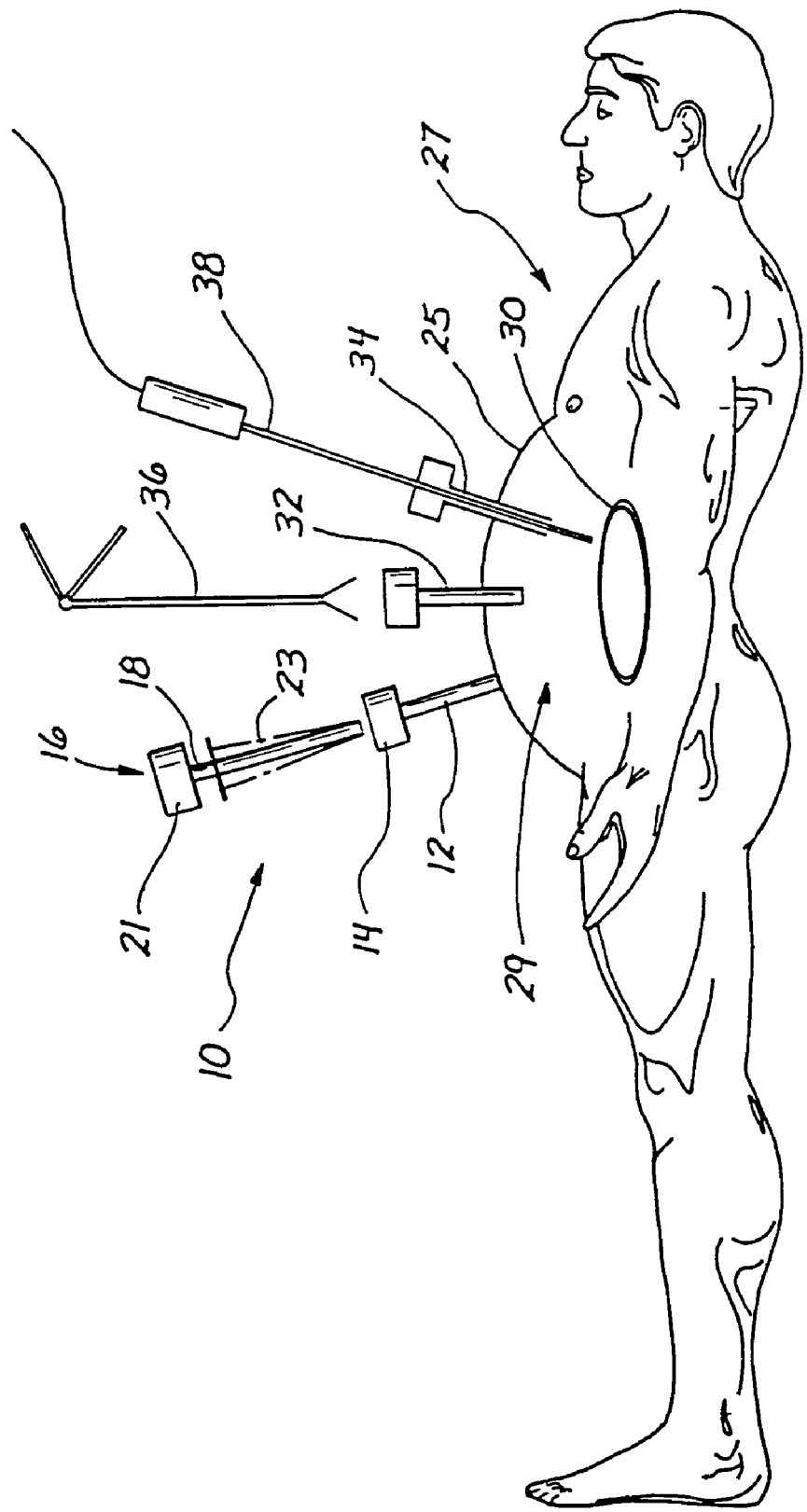
FIG. 1 is a side elevation view of a patient with insufflated abdomen and trocars in the process of being placed using the trocar system of the present invention.

A trocar system of the present invention is illustrated generally in FIG. 1 and designated by the reference numeral 10. The system 10 includes a trocar cannula 12 having a seal housing 14, and an obturator 16 with a shaft 18 and handle 21, and including a traction mechanism 23 of particular interest to the present invention. The obturator 16 is used in placing the cannula 12 across a body wall such as an abdominal wall 25, associated with a patient 27. In the case of the abdomen, the wall 25 defines an abdominal cavity 29 which includes many organs such as that designated by the reference numeral 30.

In less evasive laparoscopic procedures, multiple cannulas 32 and 34 are used to provide access across the abdominal wall 25 to facilitate surgical procedures within the abdominal cavity 29. By way of example, the removal of a gallbladder is typically accomplished with such a laparoscopic procedure. Initially, cannulas 12, 32 and 34 are placed across the abdominal wall 25, each providing a working channel through which various instruments can be inserted and surgically manipulated. For example, the cannula 32 is shown with a grasper 36 which can be inserted through the cannula to grasp the organs 30 or other tissue within the abdominal cavity 29. A fiber-optic scope 38 is illustrated in FIG. 1 operatively disposed through the cannula 34 and across the abdominal wall 25 to provide visualization within the abdominal cavity 29.

As further back-ground to the trocar system 10 of the present invention, FIGS. 2–5 are provided and to illustrate the deficiencies of trocars and obturators of the prior art.

Figure 2:
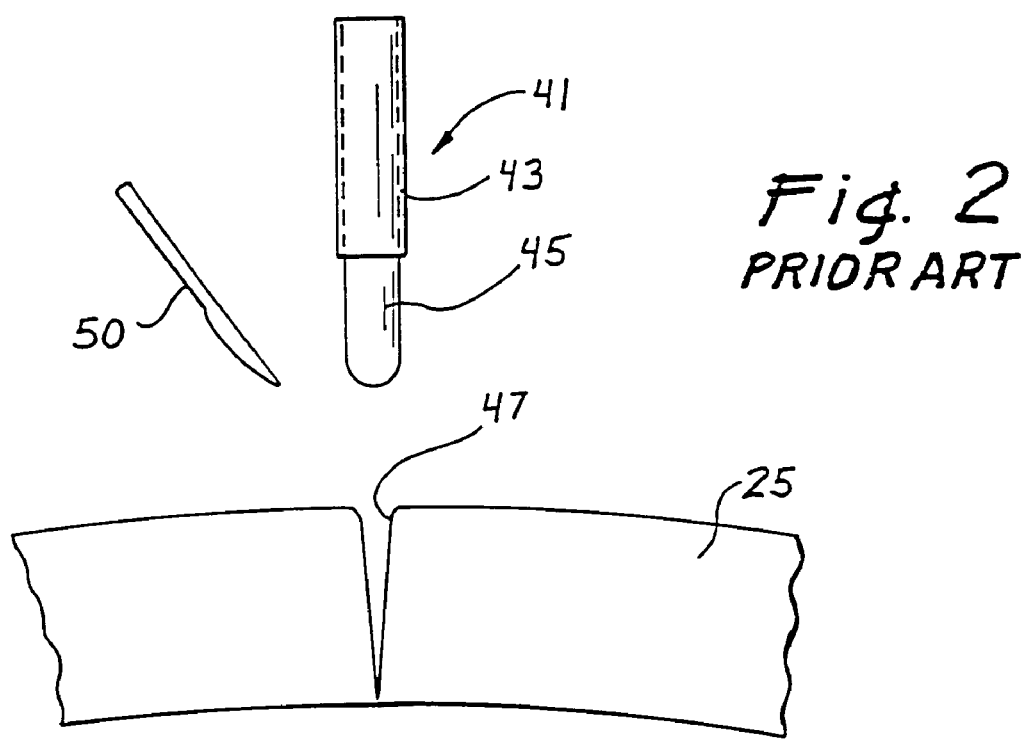
FIG. 2 is a side elevation view of a prior art trocar system involving an incision and blunt tip obturator.

One trocar of the prior art is illustrated in FIG. 2 and is designated by the reference numeral 41. This trocar includes a cannula 43 and blunt obturator 45. In the placement of this device, an incision 47 is cut entirely through the abdominal wall 25 using a scalpel 50. All of the deficiencies previously discussed with respect to cutting rather than parting the abdominal wall 25 impact this procedure. After the incision 47 is cut, the blunt obturator 45 is moved through the incision to place the cannula 43 across the wall 45. Due to the delicate cutting required by this procedure, placement of this trocar 41 may take as long as 10 minutes. In a procedure requiring the placement of four trocars, this time intensive procedure would require as much as 40 minutes, for example.

In comparison, placement of a self-cutting obturator may require only one minute of time. In a procedure requiring the placement of four trocars, this part of the procedure may require only four minutes of time as opposed to the 40 minutes of time required for the precut procedure of FIG. 2.

Figure 3:
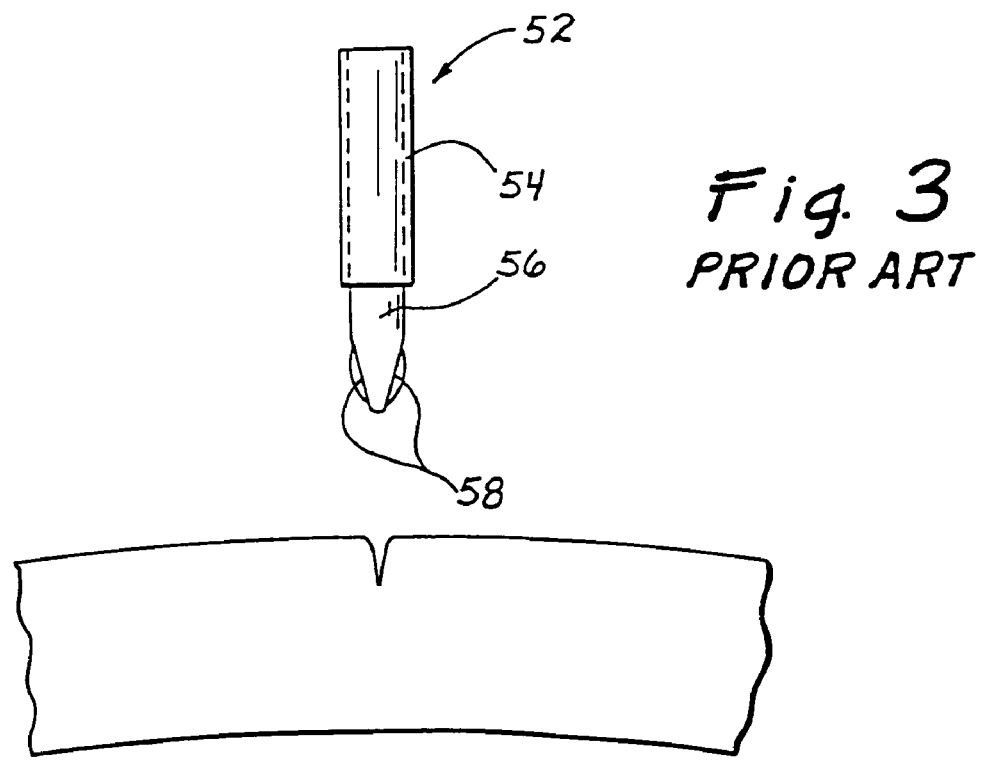
FIG. 3 is a side-elevation view of a prior art trocar system involving an obturator with cutting wings.

A self-cutting trocar system 52 of the prior art is illustrated in FIG. 3. This system 52 includes a cannula 54 and an obturator 56 having a pair of opposing wings 58. These wings 58 are provided with sharpened outer edges so that they tend to cut a path through the abdominal wall 25. Again, the disadvantage of cutting an incision through the abdominal wall 25 also impacts this embodiment.

Figure 5:
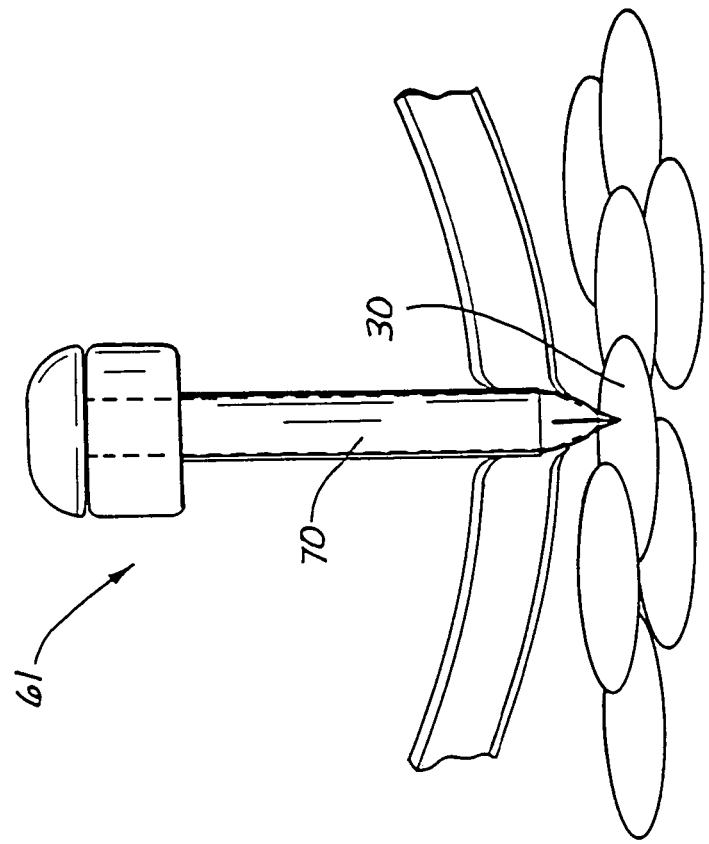
FIG. 5 is a side elevation view of the system of FIG. 4 invading an interior organ.
Figure 4:
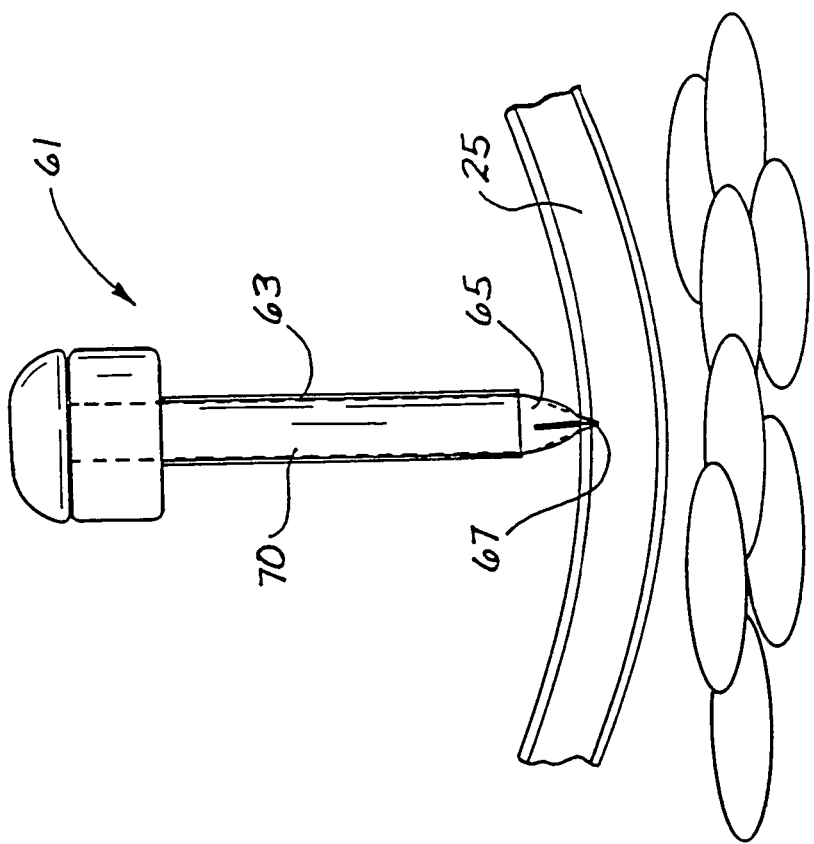
FIG. 4 is a side elevation view of a prior art trocar system including a cutting tip.

Perhaps the most widely used embodiment of a trocar is that illustrated in FIGS. 4 and 5. In this case, a trocar 61 includes a cannula 63 and obturator 65 having a sharpened point 67. A safety shield 70 associated with the obturator 65 is biased to move over the point 67 and to protect the interior organs 30 upon penetration of the abdominal wall 25. In the process associated with this instrument, the trocar 61 is forced through the abdominal wall 25 creating a significant distal force on the wall 25. This distal force provides the wall 25 with a concave shape, commonly referred to as tenting, and tends to bring the point 67 into close proximity to the interior organs 30.

As with the prior art embodiment of FIG. 3, the point 67 precedes the remainder of the trocar 61 as it cuts the tissue of the wall 25. Therefore, of the deficiencies previously discussed with reference to cutting are applicable to this prior art embodiment. Furthermore, the significant force required for penetration, a force typically as high as ten pounds, coupled with close proximity of the concave wall 25 to the organs 30, tends to provide little time for the safety shield 70 to cover the tip 67. As a consequence, damage to the interior organs 30 has been severe notwithstanding the presence of the safety shield 70.

The high forces required for penetration are particularly applicable to those trocar systems which require both penetration forces as well as cutting forces.

In all of these embodiments of the prior art, it will be noted that cutting of the abdominal wall is required. Furthermore, all forces associated with movement of the trocars 41, 52 and 61 through the abdominal wall 25 produce a distal force as great as ten pounds which tends to move the abdominal wall 25 into a concave shape and into close proximity with the interior organs 30.

The advantages of the trocar system 10 of the present invention will be readily apparent with reference to the obturator 16 of FIG. 6 and a comparison with the prior art devices illustrated in FIGS. 2–5. As previously discussed, this obturator 16 includes the shaft 18, handle 21 and traction mechanism 23. In this case, the traction mechanism 23 may include a fabric 72 having the configuration of a tube with a first end 74 and a second end 76. In this context, the word "fabric" refers to any flexible sheet material. The shaft 18 can be solid, but in a preferred embodiment it is at least partially hollow to receive the first end 74 of the fabric 72 within the shaft 18. The shaft 18 extends to a distal tip 78 having a wall 81 that defines an internal channel 83 and an axial hole 85. This wall 81 is defined by a leading surface 87.

The tubular fabric 72 is initially disposed with its first end 74 positioned in the interior channel 83. The fabric 72 extends distally outwardly through the hole 85 where it inverts and extends proximally along the leading surface 87 and the outer surface 90 of the shaft 18. At the second end 76, the tubular mesh is preferably attached to a finger engagement means, such as a projection, tab, flange or ring 92.

In operation, the handle 21 of the obturator 16 is placed in the palm of the user's hand and his/her fingers are extended to engage the ring 92. In a common and familiar motion, the hand of the user is closed drawing the fingers towards the palm of the hand. This moves the ring 92 toward the handle 21 and draws the tubular fabric 72 distally through the hole 85 and proximally along the outer surface 90 of the shaft 18. As the ring 92 moves proximally upwardly in FIG. 6, the first end 74 of the fabric 72 is pulled toward the distal tip 78 where the fabric 72 exits the hole 85 and inverts to move along the outer surface 90. With the fabric 72 disposed between the shaft 18 and the abdominal wall 25, it tends to grip the abdominal wall 25, and move the wall 25 proximally along the shaft 18. As the wall 25 moves upwardly in FIG. 6 along the shaft 18, it tends to part at the leading edge 87 along a line of weakness designated generally by the reference numeral 94. It is of particular importance to note that the wall 25 is parted rather than cut in order to achieve the advantages previously discussed. In this particular embodiment, there is no structure which works to cut the abdominal wall 25 or otherwise force the obturator 16 along a predetermined path. Rather, the obturator 16 finds its own path along the line of weakness 94.

Notwithstanding this significant aspect of the present invention, perhaps the greatest advantage is achieved with a net zero or even proximal force on the wall 25. As previously noted, the prior art produced only a distally directed force in creating an incision while moving an obturator through the abdominal wall. This tended to move the abdominal wall toward a concave shape and into proximity with the internal organs. With the present embodiment, the handle 21 can be held stationary with a distally directed force, shown by an arrow 96, while a counter proximal force of equal or greater magnitude is applied to the ring 92, as shown by the arrows 98.

Since these forces, shown by the arrows 96 and 98, are applied in different directions, they tend to offset each other so that the net distal force applied to the abdominal wall 25 can actually be negative. Note for example, that if the handle 21 is maintained stationary, and the ring 92 is moved upwardly, the net force on the abdominal wall 25 is a proximal-force directed upwardly in FIG. 6. As a result, the abdominal wall 25 can be moved toward a convex shape and a spaced relationship with the interior organs 30.

Figure 7:
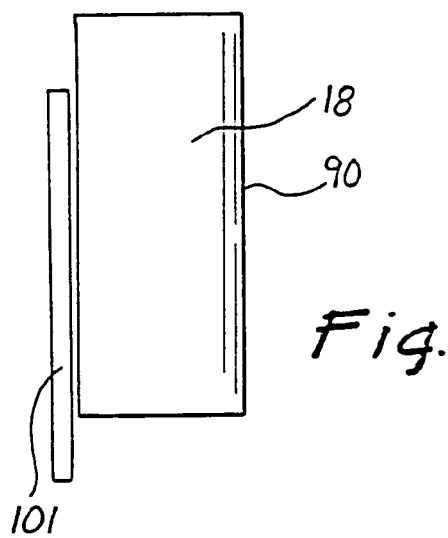
FIG. 7 is a side elevation view of an embodiment including a single traction tread.
Figure 8:
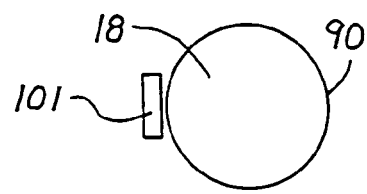
FIG. 8 is a radial cross section view taken along lines 8—8 of FIG. 7.

It will be appreciated from the foregoing discussion, that the counter forces which are of particular advantage to the present invention can be produced from a variety of structures. More specifically, the tubular fabric 72 discussed with reference to FIG. 6 can be any material capable of being pulled along the outer surface 90 of the shaft 18. This material could be organic or inorganic and will generally be elongate so that it can be pulled with some magnitude of force in the axial, proximal direction. For example, the tubular fabric 72 of FIG. 6, although preferred for that embodiment, could be replaced with just a single traction tread 101 as illustrated in FIG. 7. With this traction tread 101 disposed between the shaft 18 and the abdominal wall 25, the traction tread 101 will engage the tissue of the abdominal wall 25 and pull it proximally relative to the shaft 18.

Figure 9:
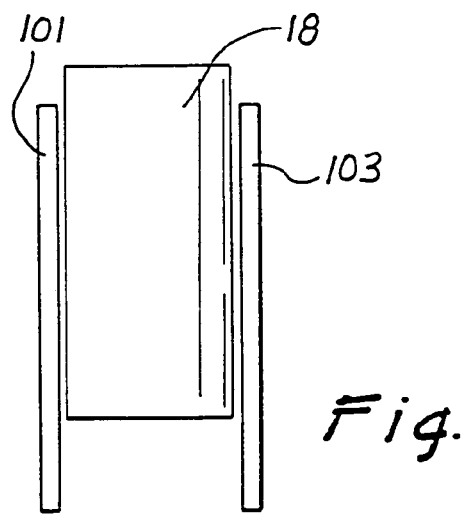
FIG. 9 is a side elevation view of an embodiment including a pair of opposing traction treads.
Figure 10:
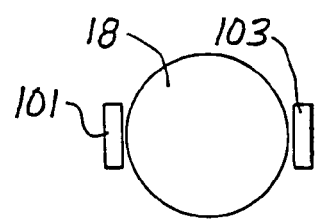
FIG. 10 is a radial cross section view taken along lines 10—10 of FIG. 9.

Forces will be more balanced if at least two traction treads, such as the tread 101 and a second tread 103, were diametrically opposed as illustrated in FIG. 9 and 10. With this configuration, the abdominal wall 25 (FIG. 1) is engaged on both sides of the shaft 18 and pulled proximally relative to the shaft 18.

Figure 11:
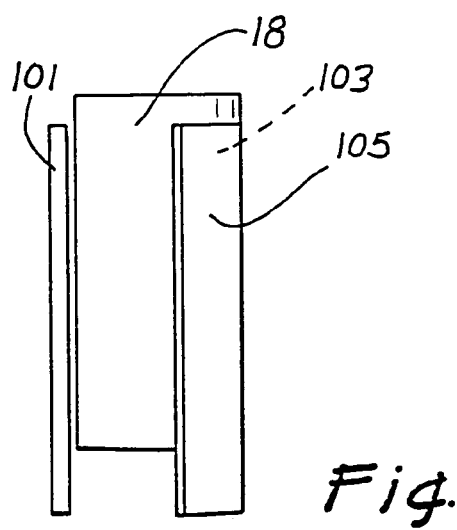
FIG. 11 is a side elevation view of an embodiment having more than two traction treads equally circumferentially spaced.
Figure 12:
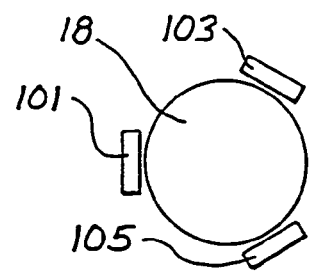
FIG. 12 is a radially cross section view taken along lines 12—12 of FIG. 11.

Other embodiments of the invention might include three traction treads, such as the treads 101 and 103 and a third tread 105, equally spaced around the circumference of the shaft 18. Such an embodiment is illustrated in FIGS. 11 and 12.

Figure 15:
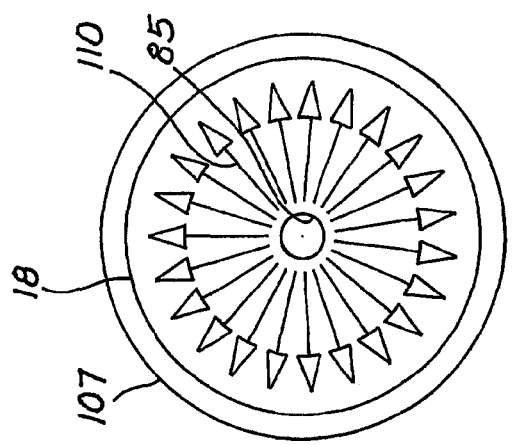
FIG. 15 is an end view taken along lines 15—15 of FIG. 14.
Figure 14:
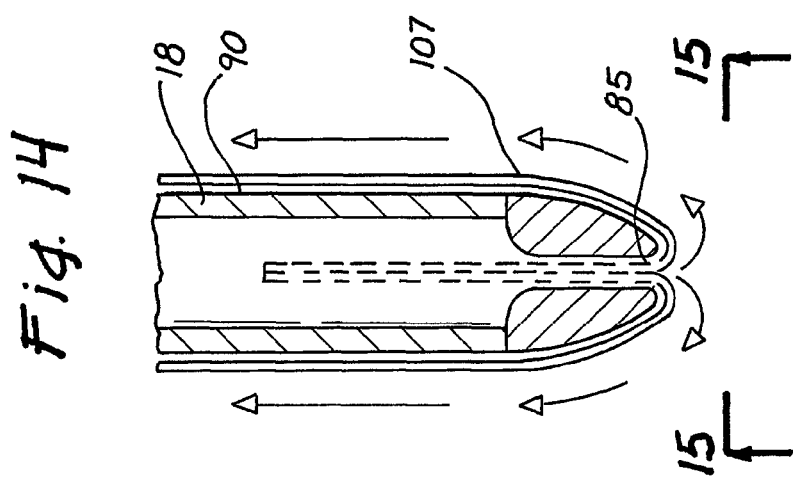
FIG. 14 is an axial cross section view taken along lines 14—14 of FIG. 13.
Figure 13:
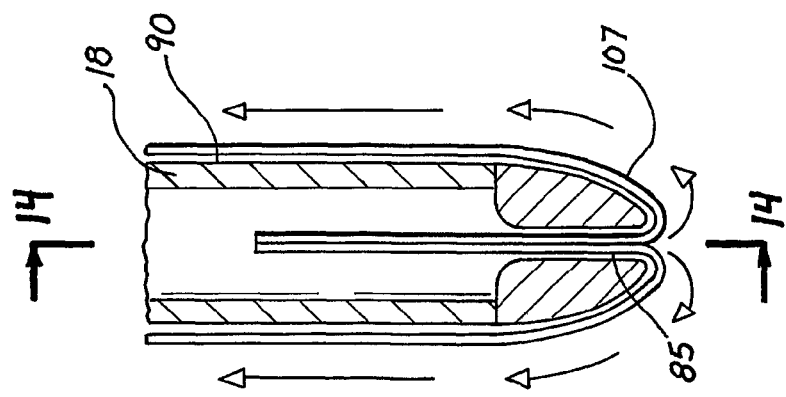
FIG. 13 is a side elevation view wherein the traction tread is radially continuous and forms a tube or traction sheath.

While independent and discrete traction treads, such as the treads 101, 103 and 105, will function to produce the discrete counter forces, a single traction tread that is radially continuous, as illustrated in FIGS. 13–15, may be preferred as it provides complete isolation of the shaft 18 from the abdominal wall 25 (FIG. 1). Where the shaft 18 of the obturator 16 is cylindrical and the distal tip 78 is conical or convex as it as illustrated in FIG. 13, this tubular configuration for the traction tread 107 is particularly desirable. With this configuration, the traction tread 107 passes through the axial hole 85 where it inverts and travels radially as shown by arrows 110 in FIG. 15. Form this point, the traction tread 107 travels proximally along the surface 90 of the shaft 18, upwardly in FIG. 14.

In a further embodiment of the invention, the distal tip 78 of the obturator 16 is formed as a pair of planar surfaces 112 and 114 which converts distally in the nature of a flathead screwdriver. This configuration lends itself to the opposing pair of tractor treads 101 and 103 previously illustrated in FIGS. 9 and 10. With this construction, the traction treads 101 and 103 separate generally at an exit slot 116 best shown in FIG. 18. In this view the opposing forces are shown by the arrows 118 and 121 which produce the tissue parting results of particular advantage to the present invention.

With reference to FIGS. 19, 20 and 21, it can be seen that a similar embodiment including the converging surfaces 112 and 114 can be accommodated with traction treads 101 and 103 which are axially continuous. Thus, each of these treads 101 and 103 forms a continuous band 123 and 125 respectively. The two bands 123, 125 counter rotate through the slot 116, and extend proximally along the surface 90, returning to the interior channel 83 through opposing windows 127 and 130 in the wall 81 of the obturator.

With respect to the embodiment of FIG. 6, the method of operation will now be discussed with reference to FIGS. 22–28. In these views, the abdominal wall 25 is further defined by a fascia 141, muscle tissue 143, and a peritoneum 145. In this case, the shaft 18 and fabric 72 of the obturator 16 can be inserted through the seal housing 14 and into the cannula 12. A distal end 132 of the cannula 12 is disposed through the ring 92 and into the associated tubular fabric 72. In operation, the trocar system 10 functions by pulling the ring 92 proximally along an outer surface 149 of the cannula 12, upwardly in FIG. 22.

In an initial step of the process, a cut 152 can be made in the skin or fascia 141. This cut 152 is preferably made to gain access to the muscle tissue 143 which is more easily parted. The cut 152 also marks the desired location for insertion of the trocar system 10. As the ring 92 is drawn upwardly along the cannula 12, the tubular fabric 72 exits the distal hole 85, inverts and follows the ring 92 upwardly along the outer surface 149. At the leading surface 187, the inverting fabric 72 produces opposing radial forces shown by arrows 154. With these opposing forces, the tissue 143 is parted along the line of weakness 94 (FIG. 6) as the trocar system 10 is moved relatively into the abdominal wall 25. It will be noted that the arrows 154 are merely representative of all of the radial forces which emanate from the hole 85 as shown by the arrows 110 in FIG. 15.

Figure 23:
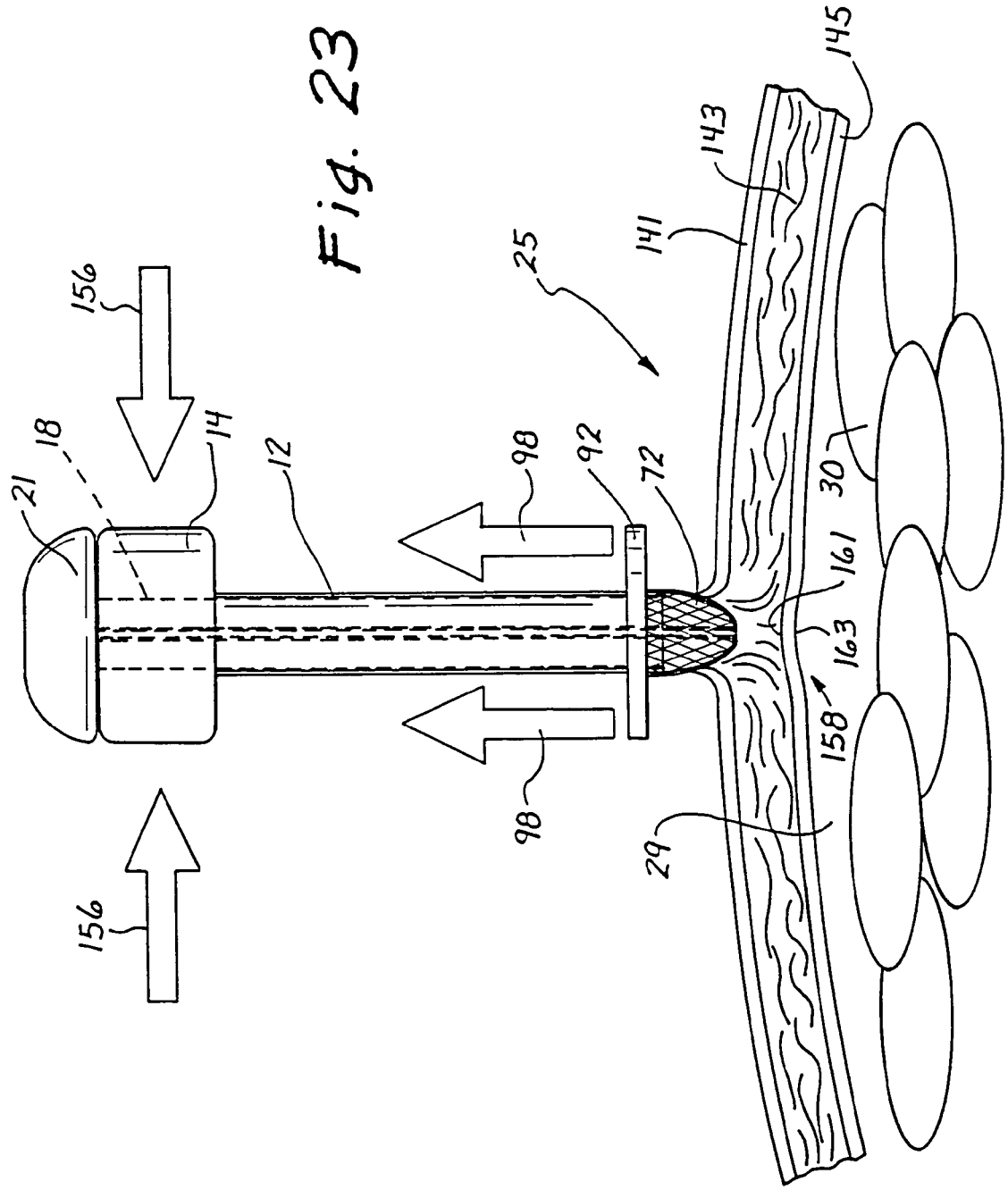
FIG. 23 is a side elevation view similar to FIG. 22 and showing the obturator with the abdominal wall being drawn upwardly onto the cannula of the trocar system.

With reference to FIG. 23, it can be seen that the ring 92 and inverted tubular fabric 72 are preferably drawn proximally by the arrows 98 while the cannula 12 and obturator 16 are held stationary as shown by a pair of arrows 156. This produces the counter forces previously described and elevates the abdominal wall 25 as it is pulled proximally upwardly along the cannula 12 by the fabric 72.

Figure 24:
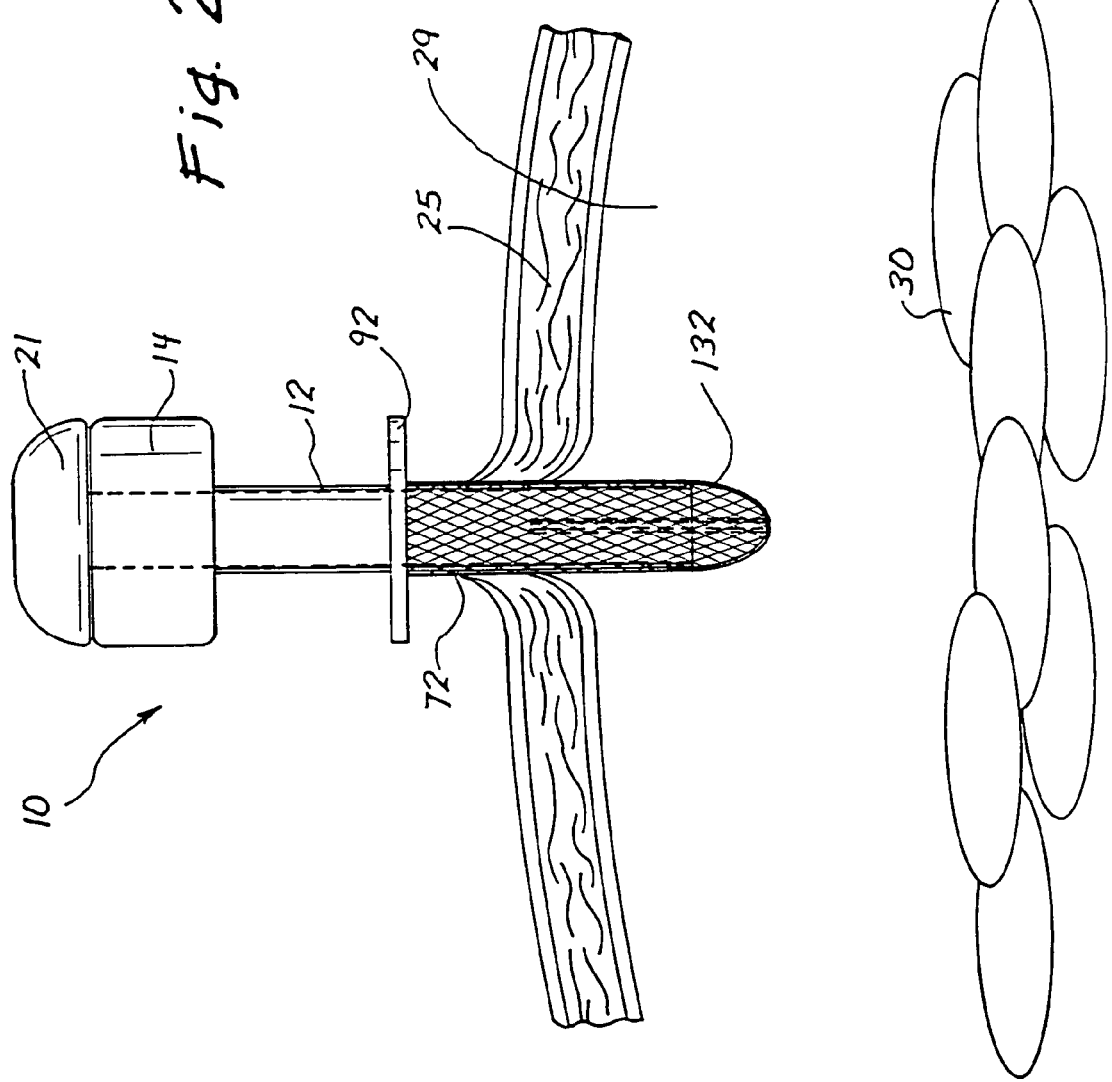
FIG. 24 is a side elevation view similar to FIG. 23 and illustrating the abdominal wall fully parted by the trocar cannula.
Figure 25:
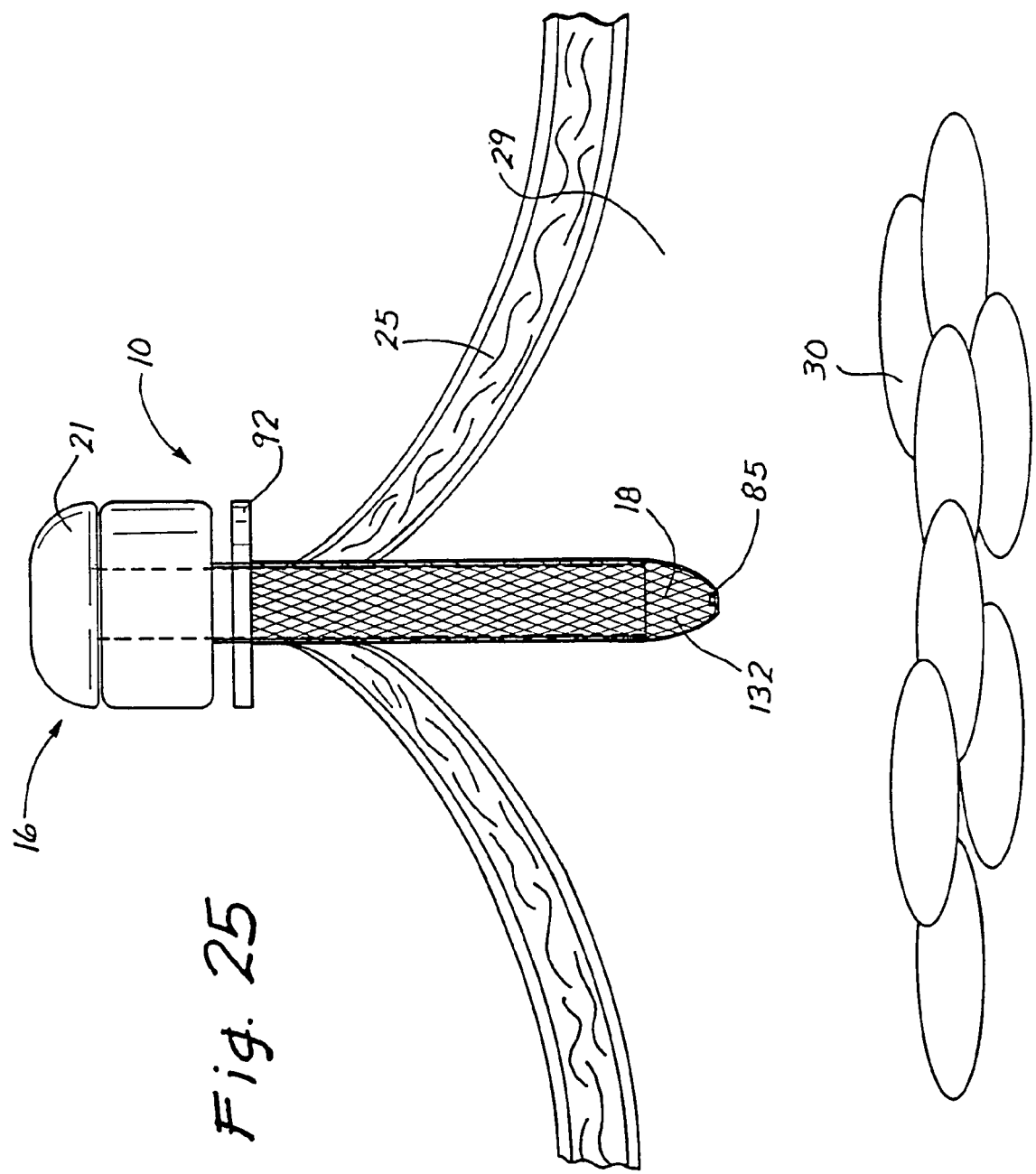
FIG. 25 is a side elevation view of the embodiment illustrated in FIG. 24 showing the abdominal wall drawn proximally onto the trocar cannula by the traction sheath.

Full penetration of the abdominal wall 25 including the peritoneum 145 is illustrated in FIG. 24. It is interesting to suspend further description at this point and note that on the distal side of the abdominal wall 25, the trocar system 10 presents no sharp objects that might be detrimental to the interior organs 30. There is no scalpel (FIG. 2), no sharp wings 56 (FIG. 3), and no sharp cutting point 67 (FIG. 5) characteristic of this prior art. Furthermore, the space between the abdominal wall 25 and the interior organs 30 is actually increased by the net proximal force associated with operation of the trocar system 10. This space can be even further increased as illustrated in FIG. 25 by merely pulling on the trocar system 10 to further elevate the convex abdominal wall 25 into a more conical configuration.

Once the trocar system 10 has fully penetrated the abdominal wall 25, the ring 92 can be drawn further upwardly along the cannula 12 into contact with the seal housing 14. In a preferred embodiment, this disposition of the ring 92 will cause the first end 74 of the tubular fabric 72 to exit the axial hole 85 of the shaft 18 (FIG. 25). At this point, the obturator 16 can be removed, leaving the seal housing 14, associated cannula 12 and tubular fabric 72. With the obturator 16 removed, the interior working channel of the cannula 12 is vacated to facilitate access with surgical instruments, such as the endoscope 38 and grasper 36 illustrated in FIG. 1.

Even during this stage of the process, the trocar system 10 of the present invention offers significant advantages. Noteworthy in this embodiment is the fact that the tubular fabric 72 remains between the cannula 12 and the abdominal wall 25 even after the obturator 16 is removed. In this position, the high traction characteristics which facilitated penetration of the abdominal wall 25 by the trocar system 10, remains to ensure that the cannula 12 stays in place during the insertion and removal of surgical instruments. The structure that aided in penetration of the abdominal wall 25 now aids in maintaining the cannula 12 in its preferred operative disposition.

Figure 26:
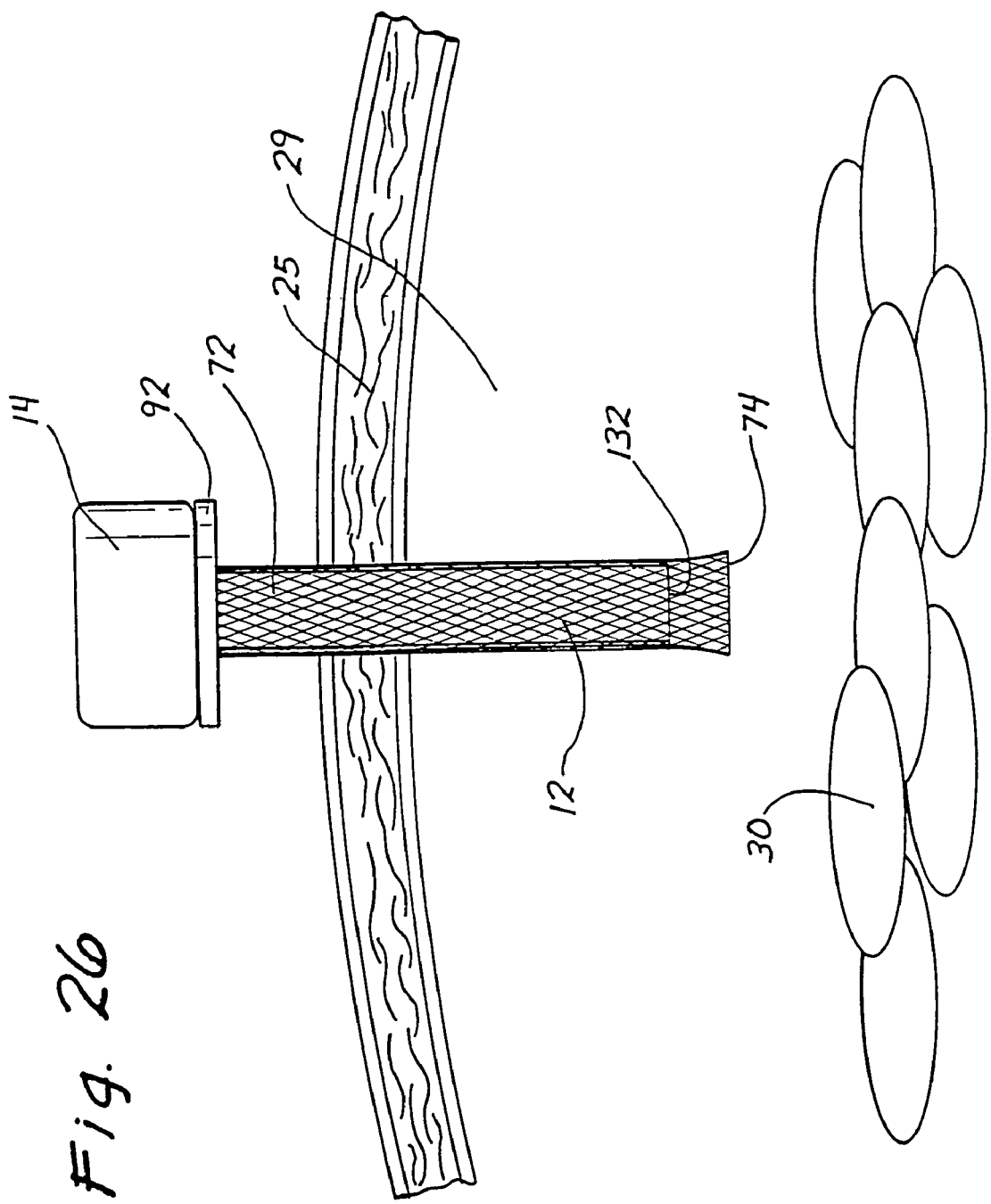
FIG. 26 is the side elevation view of the system illustrated in FIG. 25 with the traction sheath fully deployed to maintain traction between the abdominal wall and the cannula, and with the obturator removed to vacate the working channel of the cannula.

When the surgical operation is complete, the cannula 12 and associated valve housing 14 (FIG. 26) can be removed, from the ring 92 and attached tubular fabric 72. This removal of the cannula 12 may be inhibited in an embodiment wherein the tubular fabric 72 is automatically biased to a reduced profile. This bias tends to exert radial forces on the cannula increasing the amount of friction which must be overcome to separate the cannula 12 from the tubular fabric 72. In such an embodiment, it has been found that application of an axial force on the ring 92 and attached tubular fabric 72, will tend to radially expand the fabric 72. In FIG. 26, this axial force is represented by an arrow 160. With this radial expansion of the fabric 72, the cannula 12 and associated valve housing 14 can be removed from the tubular fabric 72.

Figure 27:
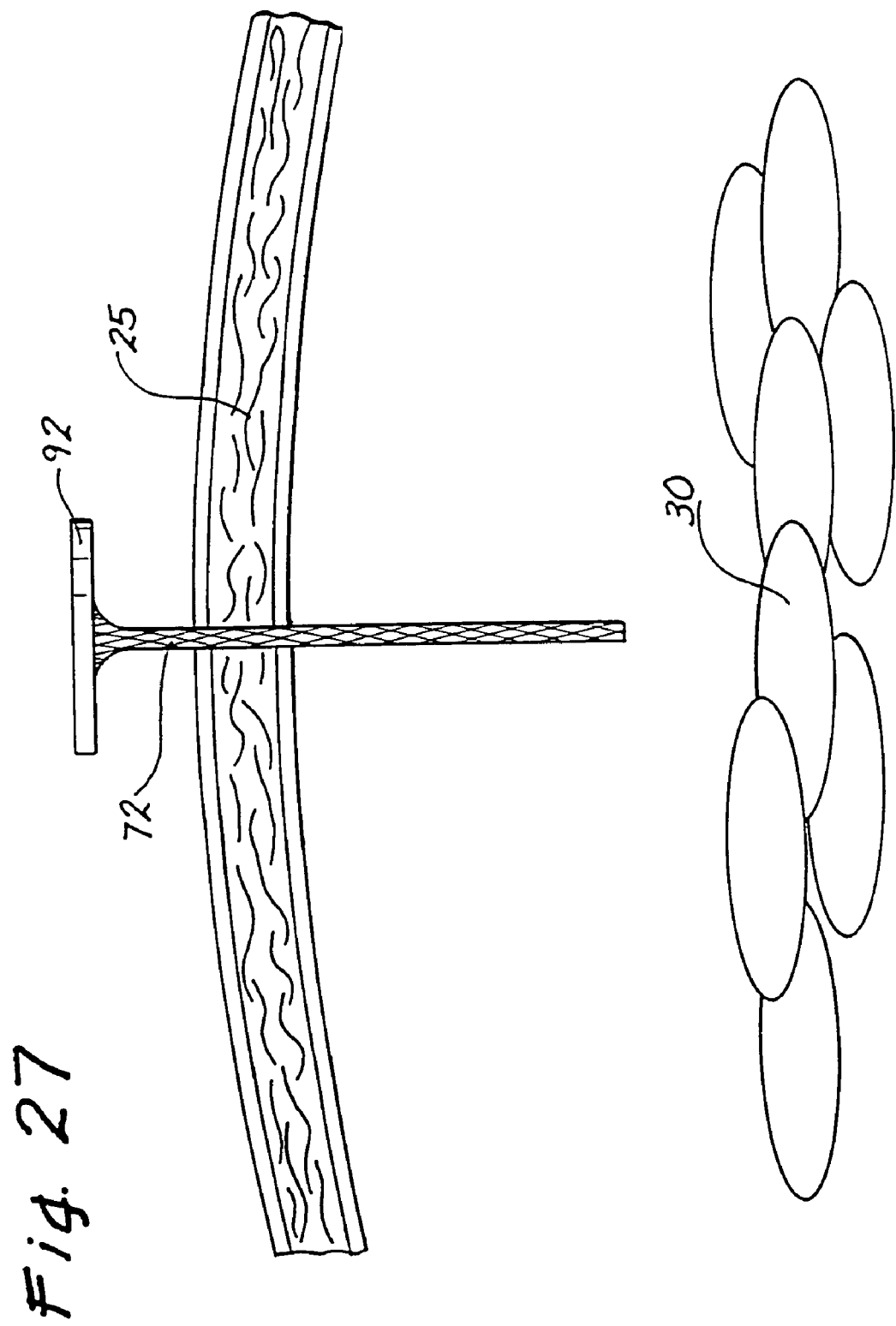
FIG. 27 is a side elevation view of the system illustrated in FIG. 26 with the trocar cannula removed from the traction sheath.
Figure 28:
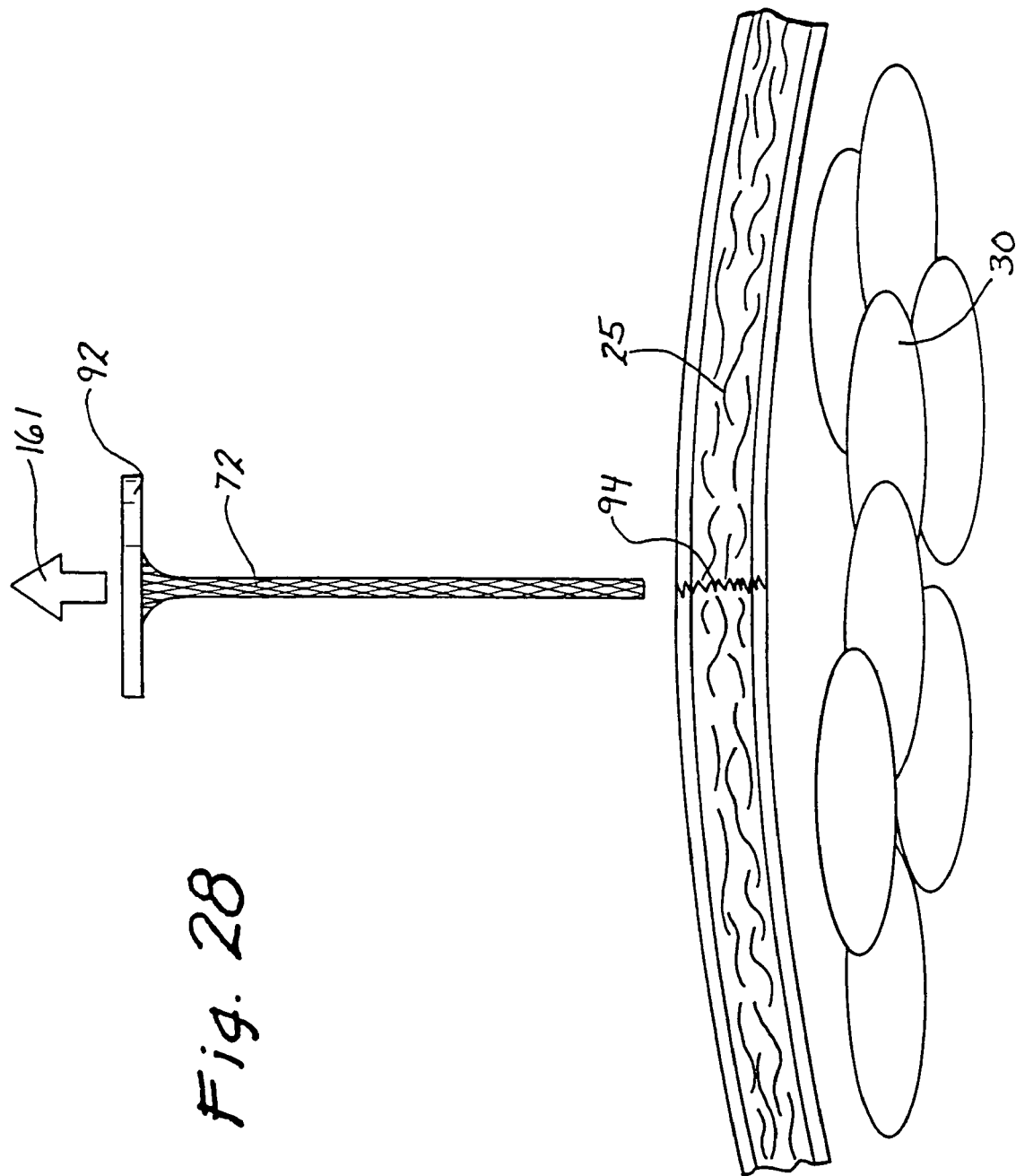
FIG. 28 is a side elevation view of the system illustrated in FIG. 27 showing the traction sheath removed from the opening leaving parted surfaces to promote healing.

Without the large cannula 12 radially stretching the fabric 72, the tubular configuration will automatically be drawn down to a reduced diameter as illustrated in FIG. 27. This lower profile greatly facilitates removal of the tubular fabric 72 as illustrated in FIG. 28 by an arrow 161. It will be noted that once the tubular fabric 72 is withdrawn, the abdominal wall 25 is left with the parted line of weakness 94 initially discussed with reference to FIG. 6.

An additional embodiment of the invention is illustrated in the progressive views of FIGS. 29–32, wherein elements of structure similar to those previously discussed are designated with the same reference numeral followed by the lower case letter "a." Thus the trocar system 10*a* is shown with the cannula 12*a* and associated seal housing 14*a*. The obturator 16*a* includes the shaft 18*a* and handle 21*a*, as well as the axial hole 85*a*. The tubular fabric is designated with a reference numeral 72*a*. Note that in this embodiment the tubular fabric 72*a* also extends through the valve housing 14*a* to the ring 92*a* which is disposed proximally of the valve housing 14*a*.

This embodiment differs from that previously disclosed in that the obturator 16*a* and tubular fabric 72*a* are disposed entirely within the working channel of the cannula 12*a*. Thus, the obturator 16*a* with fabric 72*a* is inserted into the cannula 12*a* in the initial step of operation. It will be noted that with this construction, the fabric 72*a* is exposed to the abdominal wall 25 (FIG. 1) only in a distal region 163 where the obturator shaft 19*a* is exposed distally of the end 132*a* of the cannula 12*a*. Since this region produces the parting forces represented by the arrows 154 in FIG. 22, as well as the proximal counter forces, represented by the arrows 98 in FIG. 6, this embodiment provides many of the advantages previously discussed.

In operation, the obturator 16*a* with tubular fabric 72*a* is disposed in the cannula 12*a*. The leading edge 87*a* is brought into contact with the body wall 25*a* and the ring 92*a* is drawn proximally toward the handle 21*a* as illustrated in FIG. 30. As the tubular mesh emanates from the axial hole 85*a* it inverts in the manner previously discussed pulling the abdominal wall 25*a* upwardly onto the cannula 12*a*. The ring 92*a* is drawn proximally into an abutting relationship with the handle 21*a* as illustrated in FIG. 31. At this point, the cannula 12*a* should be fully inserted through the abdominal wall 25*a*. Following this step in the surgical procedure, the obturator 16*a* as well as the tubular fabric 72*a* can be entirely withdrawn leaving the cannula 12*a* operatively disposed across the abdominal wall 25*a* as illustrated in FIG. 32.

One of the significant advantages associated with this embodiment is that the obturator 16*a* and tubular fabric 72*a* can be repeatedly used in the placement of multiple cannulas, such as the cannula 12*a*. Thus, a first cannula can be placed through the abdominal wall using the obturator 16*a*. Upon removal of the obturator 16*a*, the first cannula can be left in place as illustrated in FIG. 32. Then the obturator 16*a* can be inserted into a second cannula to facilitate its placement across the abdominal wall. The same obturator 16*a* can then be removed to facilitate placement of additional cannulas.

A further embodiment of the invention is illustrated in FIGS. 33–35 where elements of structure similar to those previously discussed are designated with the same reference numeral followed by the lower case letter "b." This embodiment is similar to that discussed with reference to FIG. 29 in that the obturator 16b and tubular fabric 72b are formed as a subassembly which is inserted into the cannula 12b. Thus, the tubular fabric 72b is only exposed in the distal region 163b distally of the distal end 132b of the cannula 12b.

The embodiment of FIG. 33 differs from that of FIG. 29 in that the tubular fabric 72b moving proximally is not disposed between the obturator shaft 18b and the cannula 12b. Rather, the proximally moving tubular fabric 72a is disposed exteriorly of the shaft 18b only in the distal region 163b. At the proximal end of this region 163b, in proximity to the distal end 132b of the cannula 12b, the proximal moving tubular fabric 72b is directed through the windows 127b and 130b back into the interior channel 83b of the shaft 18b.

Within the channel 83b, the second end 76b of the tubular fabric 72b is attached to the ring 92b. This calls for a special construction of the shaft 18b and ring 92b which is best described with reference to the radial cross section view of FIG. 34.

In order to attach the second end 76b of the tubular fabric 72b (which is disposed interiorly of the shaft 18b) to the ring 92b (which is disposed exteriorly of the shaft 82b), some structure is required to extend through the wall 81b of the shaft 18b. Initially, the shaft 18b can be formed with axial slots 165 which extend along the shaft 18b beneath the ring 92b. These axial slots 165 are preferably equally spaced around the circumference of the shaft 18b. Spokes 167 integrally molded with the ring 92b, can be positioned in the slots 165 of the shaft 18b to extend from regions exterior of the shaft 18b to regions interior of the shaft 18b. Within the channel 83b, the second end 76b of the tubular mesh can be attached to the spokes 167.

A similar embodiment of the invention is illustrated in FIG. 35 where elements of structure similar to those previously discussed are designated by the same reference numerals followed by the lower case letter "c". In this case, the obturator shaft 18c is formed at its distal end with a structure similar to that illustrated in FIG. 16. Thus, the shaft 18c is formed with the converging planar surfaces 112c and 114c and the separate traction treads 101c and 103c, best illustrated in FIG. 36. As previously discussed, this embodiment requires both of the windows 127c and 130c, as well as the slot 116c. This embodiment of the trocar system 10c offers a further advantage that the obturator 16c can be used repeatedly with multiple cannulas 12c.

For those embodiments which offer this choice of repeated use, such as the embodiments of FIGS. 29, 33 and 36, it may be desirable to provide some means for recycling the obturator 16 as illustrated in FIG. 37. In this case, a tension spring 170 is fixed at one end to the handle 21c and at the other end to the first end 74c of the tubular fabric 72c. In operation, the ring 92c is drawn proximally toward the handle 21c along with the second end 76c of the tubular fabric 72c. This causes the first end 74c of the tubular fabric 72c to move distally stretching the spring 170. The spring 170 is stretched even further (FIG. 38) as the ring 92c is drawn proximally and the traction treads 101c and 103c pass outwardly through the axial slot 116c and inwardly through the windows 127c and 130c, respectively. When this operation is completed and the associated cannula 12c is placed across the abdominal wall 25c, the obturator 16c can be withdrawn and the ring 92c released from its proximal-most position (FIG. 38). At this point, the bias of the spring 170 will pull the first ends 74c of the traction treads 101c, 103c proximally. As the obturator 16c is reset, the treads 10c, 103c will pass outwardly through the windows 127c, 130c, respectively, and inwardly through the axial slot 116c. This will enable the spring 170 to return to its normal, non-stretched state with the ring 92c disposed in its distal most position.

It can be appreciated that the spring 170 could be replaced with any biasing means which mechanically, electrically or elastomericallyo, for example, would bias the first end 74c in the proximal direction.

With the foregoing description of these preferred embodiments, it can be appreciated that the structure forming the tubular fabric 72 as well as the various traction treads 101, 103, 105 and 107, is of particular importance to the present invention. This structure is preferably formed as a sheet material and is flexible and elongate with at least one tractive surface. These characteristics will be appreciated particularly in those embodiments involving the traction treads 101 and 103 where the width of the treads remains generally constant. In these cases, the tread is able to maintain its width as it exits the distal slot 116 and enters the windows 127 and 130.

For those embodiments involving the distal exit hole 85, it may be further desirable if the structure of the fabric is capable of radially expanding and contracting. Particularly if the mesh is biased to the contracted low-profile state, it will occupy less space within the interior channel 83 and more easily feed through the exit hole 85. A bias to the contracted state will also facilitate removal of the fabric 72 as illustrated in FIG. 28.

As noted, the fabric 72 preferably has a sheet configuration and can be either woven or non-woven. It can be formed with filaments, which in the preferred embodiment of FIG. 39, are divided into filament groups 170 and 172 that extend in transverse directions. Thus the filaments in the group 170 may extend, in a normal state, perpendicular to the filaments in the group 172, as illustrated in FIG. 39.

In order to facilitate the traction characteristics of the material 168, the filament groups 170 and 172 can be woven to form points of intersection 174 where the filaments cross and spaces or interstices 176 between the filaments. At the points of intersection, the fabric 72 will have a thickness equal to the sum of the diameters of a single filament in the group 170 and a single filament in the group 172. Between the points of intersection, the filaments in the groups 170 and 172 will provide the fabric 72 with only a single thickness. In the interstices 176 between the filaments of the groups 170 and 172, the material 168 will have zero thickness. Thus, the woven configuration of even this simple embodiment will provide the fabric 72 with three different thicknesses greatly facilitating the traction between the material 168 and the tissue associated with the abdominal wall 25 (FIG. 1).

Even those significant traction characteristics can be dramatically increased with simple variations in the weave parameters. Consider for example the effect of making the various filament groups 170, 172 with different diameters. With an appropriate weave, this could add two additional levels of thickness to the fabric 72. Thus it is contemplated that any of the weaves known in the textile industry could provide multiple levels of thickness having dramatic effects on the traction of the fabric 72 relative to the tissue of the abdominal wall 25 (FIG. 1).

It should also be considered that any one of the filaments in the groups 170 and 172 can be formed from a different material. Solid, non-resilient materials, such as monofilament, will tend to maintain their shape providing more of a mechanical traction to the tissue. The filaments could also be formed from fibrous materials, such as cotton, in which case traction would be further enhanced by capillary action. The filaments of the groups 170, 172 could also be individually varied in their diameters or thicknesses, or provided with a more tractive surface, shape or coating.

In a preferred embodiment, the filaments forming the group 170 include monofilaments which are alternated with cotton filaments. The same alternation of filament materials is applied to the filaments of the group 172. With even a simple weave of these filament groups 170 and 172, significant variations in thickness occur due to the fixed diameter of the monofilaments and the variable diameter of the cotton filaments. The resulting material 168 provides many different thicknesses for high mechanical traction and additionally provides the capillary action associated with fibrous cotton material.

Thermoplastic materials can also be used for the filaments in the groups 170 and 172. These materials will permit the fabric 72 to be biased to a compacted state as illustrated in FIG. 40 and stretched to an expanded state as illustrated in FIG. 41. This thermoplastic bias facilitates movement of the tubular fabric 72 between a low profile state interiorly of the shaft 18b, and an expanded high profile state exteriorly of the shaft 18b. With a bias to the low profile state, the tubular fabric 72 will automatically contract to achieve the advantages previously discussed.

The fabric 72 can also be woven in a manner that the filaments of the group 170 are fixed to the filaments of the group 172 at each point of intersection 174. This feature will tend to make the fabric 168 more rigid so that it does not tend to close down on the surface of the cannula 12 or shaft 18 as it is drawn proximally. The resulting fabric 72 will also have less of a tendency to expand or contract. This may tend to produce pleats in the fabric 72 particularly where it emanates from the axial hole 85b. With reference to FIG. 42, it can be seen that these pleats 178 can provide the further advantage of texture variations at the critical leading surface 87 of the obturator 16. This additional texture can even further enhance the traction with the tissue where the important parting of the tissue is taking place.

Alternatively, the filaments forming the group 170 and 172 can remain disconnected at their points of intersection 74. This will enable the filaments to move over each other enhancing their ability to expand and contract. The characteristic of this weave is best illustrated in FIG. 43 where the fabric 168 tends to maintain its cylindrical configuration as it passes through the axial hole 85 and moves from the low profile state to the high profile state.

In a particular embodiment of the invention it may be desirable to control the stretchability of the fabric 168 in different directions. For example, it may be desirable to facilitate radial expansion while inhibiting axial expansion. The radial expansion might be desirable as it facilitates the transition of the tubular fabric 72 from the low profile state at the exit hole 85b, to the high profile state exteriorly of the cannula 12 or shaft 18. At the same time, it might be desirable to inhibit expansion or contraction in the axial direction. Alternatives for providing different stretch characteristics in different directions are well known in the textile industry and include formation of the fabric 72 with filaments of different material and shape as well as orientation of the filaments relative to the cut of the fabric 168.

A further embodiment of the invention is illustrated in FIG. 44 where elements of structure similar to those previously discussed are designated with the same reference numeral followed by the lower case letter "d." In the side elevation view of FIG. 44, the obturator 16d is illustrated with its wall 81b extending along an axis 181 to form a blunt tip 183 and the exit hole 85d. A needle 185 having a sharp conical tip 187 is supported within the interior channel 83d to extend slightly through the axial hole 85d. In this embodiment, the tubular mesh 82d is disposed around the needle 185 and exits through the axial hole 85d and proximally along the wall 81d in the manner previously discussed. The needle 185 can be fixed to the obturator 16b, or can be moveable distally, either manually or automatically, to facilitate penetration of the wall 25.

Figure 22:
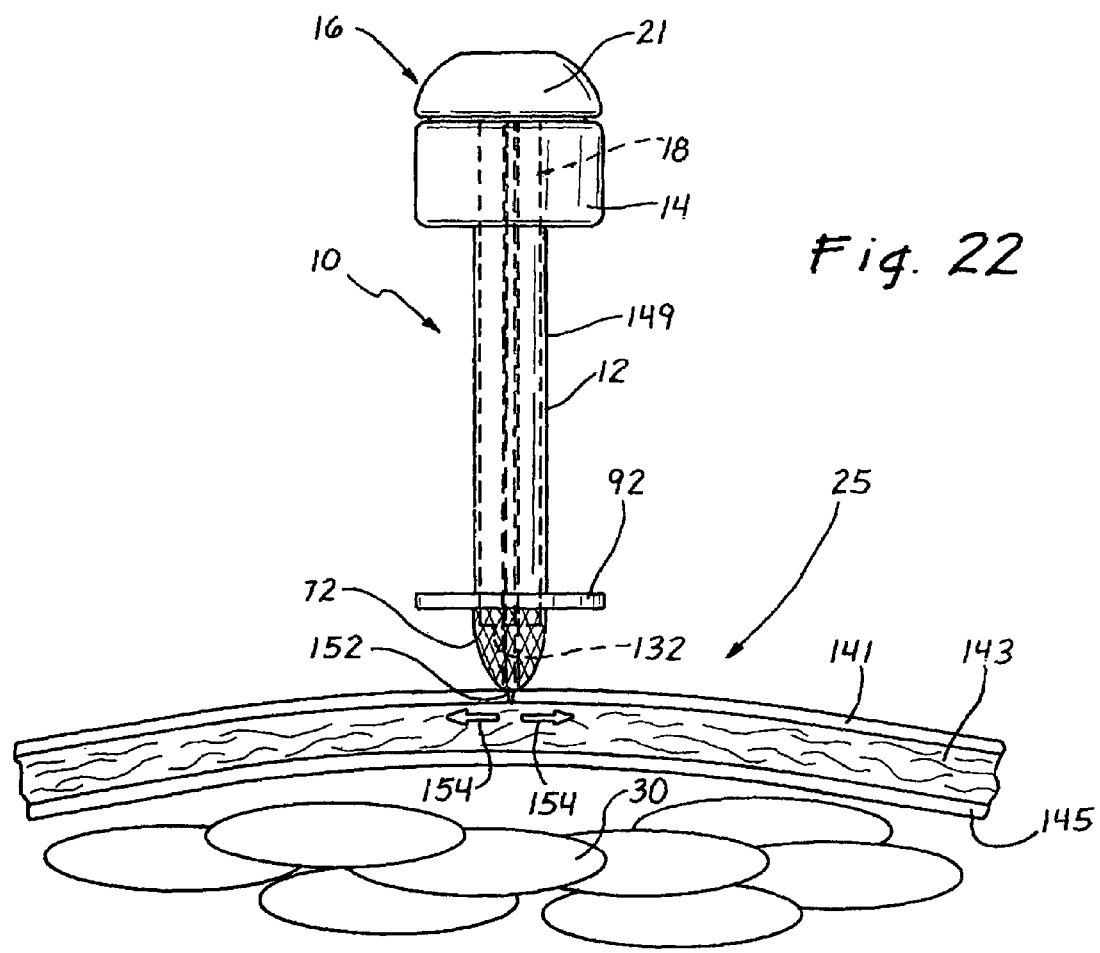
FIG. 22 is a side elevation view of the embodiment of FIG. 13 placed in initial contact with an abdominal wall to produce opposing parting forces.

With this construction, the needle 185 can provide a microscopic puncture which precedes the fabric 72d as it exits from the hole 85d. This microscopic puncture can provide the initial cut 152 in the fascia 141 and/or facilitate puncture of the peritoneum 145 (FIG. 22). Even in this embodiment it is desirable that the parting forces represented by the arrows 152 and 154 of FIG. 22 predominate over any cutting associated with the conical tip 187. This will ensure that the obturator 16 progresses along the line of weakness 94 to achieve the advantages previously discussed with reference to FIG. 6.

Figure 46:
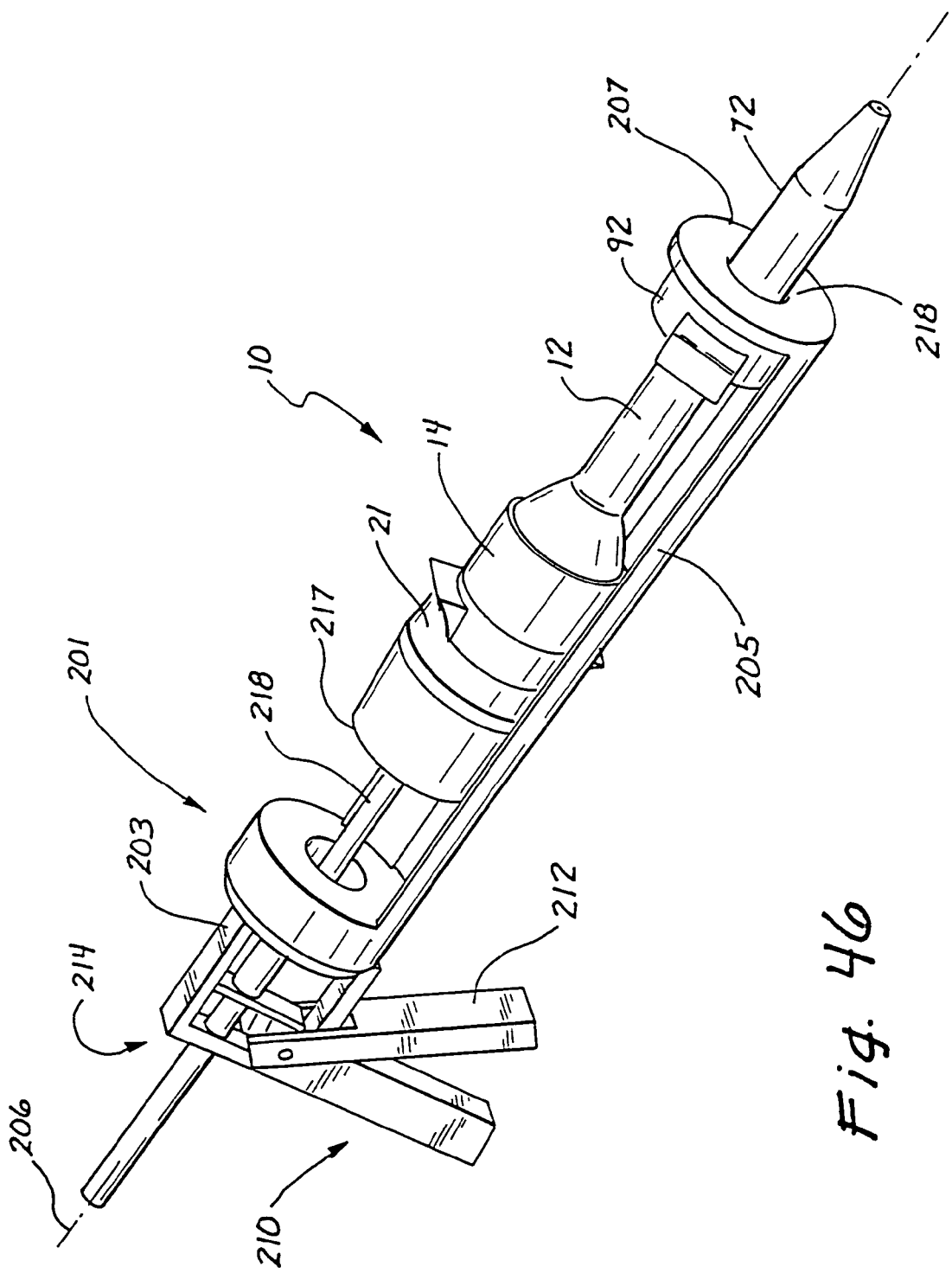
FIG. 46 is a perspective view of an application adapted for use in placing the trocar system of the present invention.

An insertion apparatus 201 adapted for use with the trocar system 10 of the present invention is illustrated in FIG. 46. This particular embodiment of the trocar system 10 includes the obturator handle 21, valve housing 14, cannula 12 and ring 92 coupled to the tubular fabric 72. The insertion apparatus 201 includes a frame 203 fixed to a longitudinal tray 205 that extends along an axis 206 to a distal radial wall 207. The frame 203 includes a palm handle 210 and finger handle 212 which operate a ratchet mechanism 214 to move a plunger 216 and a distal engagement pad along the tray 205.

In operation, the trocar system 10 is placed within the tray 205 and aligned axially with its cannula 12 extending through a hole 221 in the distal wall 207. Importantly, the ring 92 is disposed on the proximal side of the wall 207.

Mechanical, electrical, or hydraulic operation of the handles 210, 212 moves the plunger 218 axially distally bringing the engagement pad 217 into contact with the handle 21 of the trocar system 10. Further operation of the handles 210 and 212 operates the ratchet assembly 214 to move the cannula 12 distally within the tray 205 of the insertion apparatus 201. With distal movement of the ring 92 inhibited by the wall 207, the ring 92 moves proximally relative to the advancing cannula 12. This deploys the tubular fabric 72 and causes it to move proximally relative to the outer surface of the cannula 12.

Use of this insertion apparatus 201 can significantly aid in placement of the trocar system 10. It not only provides some mechanical advantage to the process but is also operable by a single hand of the user.

In a further embodiment of the invention illustrated in FIG. 47, elements of structure similar to those previously discussed are designated by the same reference numeral followed by the lower case letter "D." Thus, this embodiment includes the obturator 16b with shaft 18b having the distal tip 78b. In this embodiment, a pair of gears 230 and 234 are rotatable on the shaft 18b and disposed radially with respect to each other. Teeth 234 and 236 on the circumference of the gears 230 and 232 extend beyond the distal tip 78b and form the leading surface 87b of the obturator 16b. The teeth 234 and 236 mesh between the gears 230 and 232 so that these gears turn in opposing directions generating the parting forces illustrated by the arrows 152b and 154b. A pilot gear 138 can be used to rotate one of the gears 130, 132 which in turn rotates the opposing gear 232 or 230 respectively. The pilot gear 238 can be rotated by any suitable mechanism, such as a belt 241 receiving an applied force from the proximal end of the obturator 16b. In this case it can be seen that the traction treads mentioned with respect to previous embodiments take the form of the gear teeth 234 and 236 which are axially continuous and produce the parting forces at the leading surface 187b. An end view of this embodiment is illustrated in FIG. 48. A further embodiment of the invention is illustrated in the axial cross section view of FIG. 49 and the associated end view of FIG. 50, where elements of structure similar to those previously disclosed are designated by the same reference numeral followed by the lower case letter "E." Thus, the obturator 16e includes a single gear 243 exposed at the distal tip 78e. In this case, the idle gear 238e is rotatable by the belt 241e alternately clockwise and counter-clockwise. This oscillating movement is transferred to the gear 230e causing its teeth 234e to move back and forth at the leading surface 87e. This oscillating movement is illustrated by an arrow 245 in FIGS. 49 and 50.

Many alterations and modifications can be made to the foregoing preferred embodiments without departing from the spirit and scope of the invention. Therefore it must be understood that the illustrated embodiments have been set forth only by way of example, and should not be taken as limiting the invention. For example, notwithstanding the fact that the claims set forth below recite certain elements and combinations, it must be expressly understood that the invention includes other combinations of fewer, more or different elements, which are not disclosed above even when not initially claimed in such combinations.

In addition, the words used in this specification to describe the invention and its various embodiments are to be understood not only in the sense of their commonly defined meanings, but also in the sense of any special definitions used in this specification, which may extend beyond the scope of the commonly defined meanings. Thus if an element can be understood in the context of this specification as including more than one meaning, than its use in the claims must be understood as being generic to all possible meanings supported by the specification and by the word itself The definitions of the words or elements of the following claims are, therefore, defined in the specification to include not only the combination of the elements which are literally set forth, but all equivalent structure, material or method steps for performing substantially the same function, in substantially the same way, to obtain substantially the same way to obtain substantially the same result. In this sense it is therefore contemplated that an equivalent substitution of two or more elements may be made for any one of the elements in the claims below or that a single element may be substituted for two or more elements in a claim. Insubstantial changes from the claimed subject matter, now known or later devised, are expressly contemplated as being equivalently within the scope of the claims. Therefore, obvious substitutions now or later known to one with ordinary skill in the art are deemed to be within the scope of the defined elements.

The claims are thus to be understood to include what is specifically illustrated and described above, what is conceptually equivalent, what can be obviously substituted, and also what essentially incorporates the idea of the invention.

Many alterations and modifications can be made to the foregoing preferred embodiments without departing from the spirit and scope of the invention. Therefore it must be understood that the illustrated embodiments have been set forth only by way of example, and should not be taken as limiting the invention. For example, notwithstanding the fact that the claims set forth below recite certain elements and combinations, it must be expressly understood that the invention includes other.

The invention claimed is:

1. A surgical instrument for parting tissue within an abdominal wall retaining internal organs, comprising:
   a shaft having an outer surface and a tip;
   a mesh sheath initially contacting the body tissue generally at a point and extending proximally and stretching radially from the point along the outer surface of the shaft;
   the shaft being operable to create a distal force on the body tissue;
   the mesh sheath being biased to a low profile state and stretchable to an expanded, high profile state;
   the mesh sheath being operable to create a proximal force on the body tissue; and
   the proximal force being greater than the distal force to create a net proximal force on the abdominal wall tending to separate the abdominal wall from the internal organs as the tissue is parted.

2. A surgical instrument, comprising:
   a shaft having a tubular configuration with an outer surface, an axial channel, and a distal tip;
   a flexible mesh sheath having a tubular configuration and extending from the axial channel of the shaft through the distal tip of the shaft;
   a handle attached to the sheath exteriorly of the shaft, the handle being moveable proximally to withdraw the sheath from the channel and to progressively invert the sheath at the tip of the shaft; and
   a cannula,
   wherein the shaft forms an obturator adapted for disposition within the cannula,
   the mesh sheath being biased to a low profile state and stretchable to an expanded, high profile state, and
   the sheath is disposed to extend proximally outwardly of the obturator.

3. The surgical instrument recited in claim 2, wherein when the shaft is disposed within the cannula, the sheath is disposed to extend proximally outwardly of the obturator and the cannula.

4. The surgical instrument recited in claim 2 wherein when the shaft is disposed within the cannula, the sheath is disposed to extend proximally between the obturator and the cannula.

5. A surgical instrument, comprising:
   a shaft having a tubular configuration with an outer surface, an axial channel, and a distal tip;
   a flexible sheath having a tubular configuration and extending from the axial channel of the shaft through the distal tip of the shaft;
   a handle attached to the sheath exteriorly of the shaft, the handle being moveable proximally to withdraw the sheath from the channel and to progressively invert the sheath at the tip of the shaft; and
   a cannula,
   wherein the shaft forms an obturator adapted for disposition within the cannula,
   the shaft is disposed within the cannula, and
   the sheath is disposed to extend proximally outwardly of the obturator between the obturator and the cannula.

* * * * *